United States Patent
Casey

(10) Patent No.: US 12,274,622 B2
(45) Date of Patent: Apr. 15, 2025

(54) SYSTEMS AND METHODS FOR ORTHOPEDIC IMPLANTS

(71) Applicant: Carlsmed, Inc., Carlsbad, CA (US)

(72) Inventor: Niall Patrick Casey, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

(21) Appl. No.: 18/754,123

(22) Filed: Jun. 25, 2024

(65) Prior Publication Data

US 2024/0341960 A1 Oct. 17, 2024

Related U.S. Application Data

(63) Continuation of application No. 16/699,447, filed on Nov. 29, 2019, now Pat. No. 12,133,803.

(Continued)

(51) Int. Cl.
G06T 15/00 (2011.01)
A61F 2/30 (2006.01)
(Continued)

(52) U.S. Cl.
CPC .......... *A61F 2/30942* (2013.01); *G06F 30/10* (2020.01); *G16H 20/40* (2018.01);
(Continued)

(58) Field of Classification Search
CPC ... A61B 17/70; A61B 34/10; A61B 2034/105; A61B 2034/108; A61B 2017/00955; A61B 2017/00526; A61B 17/7074; A61B 2017/00982; A61B 2034/102; A61B 2034/104; B33Y 50/00; B33Y 80/00; A61F 2002/30952; A61F 2111/16; G06F 30/10
(Continued)

(56) References Cited

U.S. PATENT DOCUMENTS 4,704,686 A 11/1987 Aldinger
4,936,862 A 6/1990 Walker et al.
(Continued)

FOREIGN PATENT DOCUMENTS

CN 104318009 A 1/2015
CN 104353121 A 2/2015
(Continued)

OTHER PUBLICATIONS

Godil SS, Parker SL, Zuckerman SL, Mendenhall SK, Devin CJ, Asher AL, McGirt MJ. Determining the quality and effectiveness of surgical spine care: patient satisfaction is not a valid proxy. The Spine Journal: Official Journal of the North American Spine Society. May 16, 2013;13(9):1006-12.*
(Continued)

*Primary Examiner* — Phu K Nguyen
(74) *Attorney, Agent, or Firm* — Perkins Coie LLP

(57) ABSTRACT

A computer-implemented method for designing a patient-specific orthopedic implant can include creating a user account associated with a patient. A patient-specific orthopedic implant can be designed based on patient data and imaging data. A healthcare provider can provide feedback for a design of the patient-specific orthopedic implant, treatment protocol, or other aspects of treatment. The patient can provide data and feedback.

36 Claims, 11 Drawing Sheets

Related U.S. Application Data

(60) Provisional application No. 62/773,127, filed on Nov. 29, 2018.

(51) Int. Cl.
*G06F 30/10* (2020.01)
*G16H 20/40* (2018.01)
*G16H 30/20* (2018.01)
*A61B 34/10* (2016.01)
*G06F 111/16* (2020.01)

(52) U.S. Cl.
CPC ........ *G16H 30/20* (2018.01); *A61B 2034/105* (2016.02); *A61B 2034/108* (2016.02); *A61F 2002/30948* (2013.01); *A61F 2002/30952* (2013.01); *A61F 2002/30962* (2013.01); *A61F 2002/3097* (2013.01); *A61F 2002/30971* (2013.01); *A61F 2002/30985* (2013.01); *G06F 2111/16* (2020.01)

(58) Field of Classification Search
USPC ........................................................ 345/418
See application file for complete search history.

(56) References Cited

U.S. PATENT DOCUMENTS

| | | |
|---|---|---|
| 5,431,562 A | 7/1995 | Andreiko et al. |
| D420,995 S | 2/2000 | Imamura |
| D436,580 S | 1/2001 | Navano |
| 6,315,553 B1 | 11/2001 | Sachdeva |
| 6,540,512 B1 | 4/2003 | Sachdeva |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 | 12/2005 | Christensen |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano |
| 7,747,305 B2 | 6/2010 | Dean et al. |
| 7,756,314 B2 | 7/2010 | Karau et al. |
| 7,799,077 B2 | 9/2010 | Lang |
| D633,514 S | 3/2011 | Tokunaga |
| D656,153 S | 3/2012 | Imamura |
| 8,214,016 B2 | 7/2012 | Lavallee |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| D735,231 S | 7/2015 | Omiya |
| D737,309 S | 8/2015 | Kito |
| 9,198,678 B2 | 12/2015 | Frey et al. |
| 9,208,558 B2 | 12/2015 | Dean |
| D757,025 S | 5/2016 | Kim |
| D761,842 S | 7/2016 | Johnson |
| 9,411,939 B2 | 8/2016 | Furrer |
| 9,445,907 B2 | 9/2016 | Meridew |
| 9,452,050 B2 | 9/2016 | Miles et al. |
| D774,076 S | 12/2016 | Fuller |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| D797,760 S | 9/2017 | Tsujimura |
| D797,766 S | 9/2017 | Ibsies |
| D798,312 S | 9/2017 | Tsujimura |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado |
| 9,993,341 B2 | 6/2018 | Vanasse |
| 10,034,676 B2 | 7/2018 | Donner |
| D825,605 S | 8/2018 | Jann |
| D826,977 S | 8/2018 | Nakajima |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| D854,560 S | 7/2019 | Field |
| D854,561 S | 7/2019 | Field |
| 10,390,958 B2 | 8/2019 | Maclennan |
| D860,237 S | 9/2019 | Li |
| D860,238 S | 9/2019 | Bhardwaj |
| D866,577 S | 11/2019 | Eisert |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D876,462 S | 2/2020 | Li |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| 11,112,770 B2 | 9/2021 | Roh et al. |
| D933,692 S | 10/2021 | Smith |
| 11,166,764 B2 | 11/2021 | Roh et al. |

(56) References Cited

U.S. PATENT DOCUMENTS

| | | |
|---|---|---|
| 11,185,369 B2 | 11/2021 | Ryan |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| 11,278,413 B1 | 3/2022 | Lang |
| D958,151 S | 7/2022 | Casey et al. |
| 11,376,076 B2 | 7/2022 | Casey et al. |
| 11,432,943 B2 | 9/2022 | Casey et al. |
| 11,439,514 B2 | 9/2022 | Casey et al. |
| 11,443,838 B1 | 9/2022 | Cordonnier |
| 11,497,559 B1 | 11/2022 | Roh et al. |
| 11,678,938 B2 | 6/2023 | Casey et al. |
| 11,696,833 B2 | 7/2023 | Casey et al. |
| 11,806,241 B1 * | 11/2023 | Hussain ............. A61F 2/30942 |
| 11,857,264 B2 | 1/2024 | Roh et al. |
| 2004/0104512 A1 | 6/2004 | Eidenschink |
| 2005/0277934 A1 | 12/2005 | Vardiman |
| 2007/0272747 A1 | 11/2007 | Woods et al. |
| 2007/0276501 A1 | 11/2007 | Betz |
| 2008/0227047 A1 | 9/2008 | Lowe |
| 2008/0294265 A1 | 11/2008 | Warkentine et al. |
| 2009/0062739 A1 | 3/2009 | Anderson |
| 2010/0100011 A1 | 4/2010 | Roche |
| 2010/0191088 A1 | 7/2010 | Anderson et al. |
| 2010/0217336 A1 | 8/2010 | Crawford et al. |
| 2010/0324692 A1 | 12/2010 | Uthgenannt |
| 2011/0269104 A1 | 11/2011 | Berckmans |
| 2012/0150243 A9 | 6/2012 | Crawford et al. |
| 2012/0296433 A1 | 11/2012 | Farin |
| 2012/0310364 A1 | 12/2012 | Li et al. |
| 2012/0322018 A1 | 12/2012 | Lowe |
| 2013/0323669 A1 | 12/2013 | Lowe |
| 2014/0072608 A1 | 3/2014 | Karagkiozaki |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0135940 A1 | 5/2014 | Goldstein |
| 2014/0164022 A1 | 6/2014 | Reed |
| 2014/0263674 A1 | 9/2014 | Cerveny |
| 2014/0272881 A1 | 9/2014 | Barsoum |
| 2014/0350614 A1 | 11/2014 | Frey |
| 2015/0079533 A1 | 3/2015 | Lowe |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0332018 A1 | 11/2015 | Rosen |
| 2016/0001039 A1 | 1/2016 | Armour et al. |
| 2016/0012753 A1 | 1/2016 | Mehdian |
| 2016/0015465 A1 | 1/2016 | Steines et al. |
| 2016/0030067 A1 | 2/2016 | Frey et al. |
| 2016/0074048 A1 | 3/2016 | Pavlovskaia |
| 2016/0117817 A1 | 4/2016 | Seel |
| 2016/0143744 A1 | 5/2016 | Bojarski et al. |
| 2016/0184054 A1 | 6/2016 | Lowe |
| 2016/0191887 A1 | 6/2016 | Casas |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0361025 A1 | 12/2016 | Reicher |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0046486 A1 | 2/2017 | Cunningham |
| 2017/0061375 A1 | 3/2017 | Laster |
| 2017/0068792 A1 | 3/2017 | Reiner |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0216047 A1 | 8/2017 | Hawkes et al. |
| 2017/0220740 A1 | 8/2017 | D'Urso |
| 2017/0242107 A1 | 8/2017 | Dussan et al. |
| 2017/0252107 A1 | 9/2017 | Turner et al. |
| 2017/0258526 A1 | 9/2017 | Lang |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0360358 A1 * | 12/2017 | Amiot ................. A61B 5/686 |
| 2017/0367645 A1 | 12/2017 | Klinder |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold |
| 2018/0168731 A1 | 6/2018 | Reid |
| 2018/0185075 A1 | 7/2018 | She |
| 2018/0233222 A1 | 8/2018 | Daley |
| 2018/0233225 A1 | 8/2018 | Experton |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0325599 A1 | 11/2018 | Sec |
| 2018/0338841 A1 | 11/2018 | Miller et al. |
| 2019/0065685 A1 | 2/2019 | Pickover |
| 2019/0069956 A1 | 3/2019 | Ryan et al. |
| 2019/0088371 A1 | 3/2019 | Casey et al. |
| 2019/0099221 A1 | 4/2019 | Schmidt et al. |
| 2019/0201106 A1 | 7/2019 | Siemionow |
| 2019/0262084 A1 | 8/2019 | Roh et al. |
| 2019/0266597 A1 | 8/2019 | Mohtar |
| 2019/0321132 A1 * | 10/2019 | Weir .................... A61B 50/33 |
| 2019/0328929 A1 | 10/2019 | Kugler et al. |
| 2019/0333622 A1 | 10/2019 | Levin |
| 2019/0354693 A1 | 11/2019 | Yoon |
| 2019/0380792 A1 | 12/2019 | Poltaretskyi et al. |
| 2020/0021570 A1 | 1/2020 | Lin |
| 2020/0085509 A1 | 3/2020 | Roh et al. |
| 2020/0170802 A1 * | 6/2020 | Casey ................. A61F 2/30942 |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2021/0059822 A1 | 3/2021 | Casey et al. |
| 2021/0064605 A1 | 3/2021 | Balint |
| 2021/0145519 A1 | 5/2021 | Mosnier et al. |
| 2021/0169576 A1 | 6/2021 | Ryan et al. |
| 2021/0210189 A1 | 7/2021 | Casey et al. |
| 2021/0287770 A1 | 9/2021 | Anderson |
| 2021/0290319 A1 | 9/2021 | Poltaretskyi et al. |
| 2021/0382457 A1 | 12/2021 | Roh et al. |
| 2022/0000625 A1 | 1/2022 | Cordonnier |
| 2022/0006642 A1 | 1/2022 | Maj et al. |
| 2022/0013211 A1 | 1/2022 | Steinberg et al. |
| 2022/0039965 A1 | 2/2022 | Casey et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |
| 2022/0313362 A1 | 10/2022 | Casey et al. |
| 2022/0387191 A1 | 12/2022 | Cordonnier |
| 2022/0401150 A1 | 12/2022 | Cordonnier |
| 2022/0409140 A1 | 12/2022 | Cordonnier |
| 2023/0014384 A1 | 1/2023 | Cordonnier |
| 2023/0023440 A1 | 1/2023 | Casey et al. |
| 2023/0034731 A1 | 2/2023 | Cordonnier |
| 2023/0052263 A1 | 2/2023 | Casey et al. |
| 2023/0067537 A1 | 3/2023 | Casey et al. |
| 2023/0086886 A1 | 3/2023 | Casey et al. |
| 2023/0087107 A1 | 3/2023 | Casey et al. |
| 2023/0136813 A1 | 5/2023 | Cordonnier |
| 2023/0138162 A1 * | 5/2023 | Winston ............... A61F 2/3094 |
| | | 700/98 |
| 2023/0268040 A1 | 8/2023 | Cordonnier |

(56) References Cited

U.S. PATENT DOCUMENTS

| | | |
|---|---|---|
| 2024/0016547 A1 | 1/2024 | Casey et al. |
| 2024/0016614 A1 | 1/2024 | Casey et al. |
| 2024/0065767 A1* | 2/2024 | Cordonnier ............ G16H 20/40 |
| 2024/0079114 A1 | 3/2024 | Casey et al. |
| 2024/0138919 A1 | 5/2024 | Casey et al. |
| 2024/0138921 A1 | 5/2024 | Roh et al. |
| 2024/0261029 A1* | 8/2024 | Casey ................... A61F 2/4611 |

FOREIGN PATENT DOCUMENTS

| | | | |
|---|---|---|---|
| CN | 204468348 | U | 7/2015 |
| CN | 105796214 | A | 7/2016 |
| CN | 106202861 | A | 12/2016 |
| CN | 107220933 | A | 9/2017 |
| CN | 108670506 | A | 10/2018 |
| CN | 110575289 | A | 12/2019 |
| CN | 111281613 | A | 6/2020 |
| CN | 112155792 | A | 1/2021 |
| CN | 113643790 | A | 11/2021 |
| EP | 3120796 | A1 | 1/2017 |
| JP | 2011517996 | A | 6/2011 |
| JP | 2012531265 | A | 12/2012 |
| JP | 2016536051 | A | 11/2016 |
| JP | 2016540610 | A | 12/2016 |
| WO | 9507509 | A1 | 3/1995 |
| WO | 2004110309 | A2 | 12/2004 |
| WO | 2008027549 | A2 | 3/2008 |
| WO | 2010151564 | A1 | 12/2010 |
| WO | 2011080260 | A1 | 7/2011 |
| WO | 2012154534 | A1 | 11/2012 |
| WO | 2014145267 | A1 | 9/2014 |
| WO | 2014180972 | A2 | 11/2014 |
| WO | 2015075423 | A2 | 5/2015 |
| WO | 2016102025 | A1 | 6/2016 |
| WO | 2016172694 | A1 | 10/2016 |
| WO | 2018193316 | A2 | 10/2018 |
| WO | 2019112917 | A1 | 6/2019 |
| WO | 2019148154 | A1 | 8/2019 |
| WO | 2022045956 | A1 | 3/2022 |

OTHER PUBLICATIONS

Clement RC, Welander A, Stowell C, Cha TD, Chen JL, Davies M, Fairbank JC, Foley KT, Gehrchen M, Hagg O, Jacobs WC. A proposed set of metrics for standardized outcome reporting in the management of low back pain. Acta orthopaedica. Sep. 3, 2015;86(5):523-33.*

Hartzler AL, Chaudhuri S, Fey BC, Flum DR, Lavallee D. Integrating patient-reported outcomes into spine surgical care through visual dashboards: lessons learned from human-centered design. eGEMs. 2015;3(2).*

Endo, Kenji et al. "Measurement of whole spine sagittal alignment using the SLOT radiography of the Sonialvision safire series clinical application." Medical Now, No. 78; Aug. 2015, 4 pages.

Eshkalak, S.K. et al., "The role of three-dimensional printing in healthcare and medicine." Materials and Design 194, Jul. 10, 20202, 15 pages.

Examination Report for European Application No. 19890663.8, mailed Feb. 7, 2024, 4 pages.

Examination Report for European Application No. 19859930.0, mailed Mar. 12, 2024, 5 pages.

Extended European Search Report for European Application No. 18885367.5, mailed Aug. 16, 2021, 8 pages.

Extended European Search Report for European Application No. 19859930.0, mailed Jun. 22, 2022, 7 pages.

Extended European Search Report for European Application No. 19890663.8, mailed Jul. 29, 2022, 8 pages.

Extended European Search Report for European Application No. 21738283.7, mailed Jan. 2, 2024, 9 pages.

Hammoudeh J.A. et al., "Current Status of Surgical Planning for Orthognathic Surgery: Traditional Methods versus 3D Surgical Planning." PRS Global Open, Feb. 2015, 11 pages.

Harrysson, O. et al., "Custom-designed orthopedic implants evaluated using finite element analysis of patient-specific computed tomography data: femoral-component case study." BMC Musculoskeletal Disorders. Dec. 2007, 8:91, 10 pages.

International Search Report and Written Opinion for International Application No. PCT/US19/50885, mailed Jan. 28, 2020, 21 pages.

International Search Report and Written Opinion for International Application No. PCT/US19/63855, mailed Feb. 14, 2020, 15 pages.

International Search Report and Written Opinion for International Application No. PCT/US22/37640, mailed Nov. 15, 2022, 13 pages.

International Search Report and Written Opinion for International Patent Application No. PCT/US2018/063530, mailed Feb. 12, 2019, 16 pages.

International Search Report and Written Opinion for International Patent Application No. PCT/US21/12065, mailed Apr. 29, 2021, 19 pages.

International Search Report and Written Opinion for International Patent Application No. PCT/US23/36137, mailed Mar. 5, 2024, 20 pages.

Majdouline et al., "Preoperative assessment and evaluation of instrumentation strategies for the treatment of adolescent idiopathic scoliosis: computer simulation and optimization." Scoliosis 7, 21 (2012), pp. 1-8.

Mangano C. et al., "Combining Intraoral Scans, Cone Beam Computed Tomography and Face Scans: The Virtual Patient." Journal of Craniofacial Surgery, Nov. 1, 2018:29(8): 27 pages.

Materialise Mimics, "Efficiently turn scans into accurate virtual 3D models," Retrieved on Nov. 1, 2019 at www. materialize.com/en/medical/software/mimics, 1 page.

Office Action for Japanese Application No. 2020-550591, mailed Dec. 26, 2022, 4 pages, English Translation.

Office Action for Japanese Application No. 2020-550591, mailed Sep. 21, 2023, 4 pages, English Translation.

Office Action for Japanese Application No. 2021-539471, mailed Aug. 3, 2023, 5 pages, English Translation.

Office Action for Japanese Application No. 2021-539471, mailed May 30, 2024, 4 pages, English Translation.

Office Action for Japanese Application No. 2021-531331, mailed Oct. 23, 2023, 2 pages, English Translation.

Pimenta, Dr. Luiz, "Current Surgical Strategies to Restore Proper Sagittal Alignment," Journal of Spine 2015, vol. 4, Issue 4, 2 pages.

Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.

Swennen, G.R.J. et al., "Three-Dimensional Treatment Planning of Orthognathic Surgery in the Era of Virtual Imaging." American Assoc. of Oral and Maxillofacial Surgeons 67:2080-2092, 2009.

Office Action for Japanese Application No. 2022-541805, mailed Jul. 25, 2024, 6 pages, English Translation.

* cited by examiner

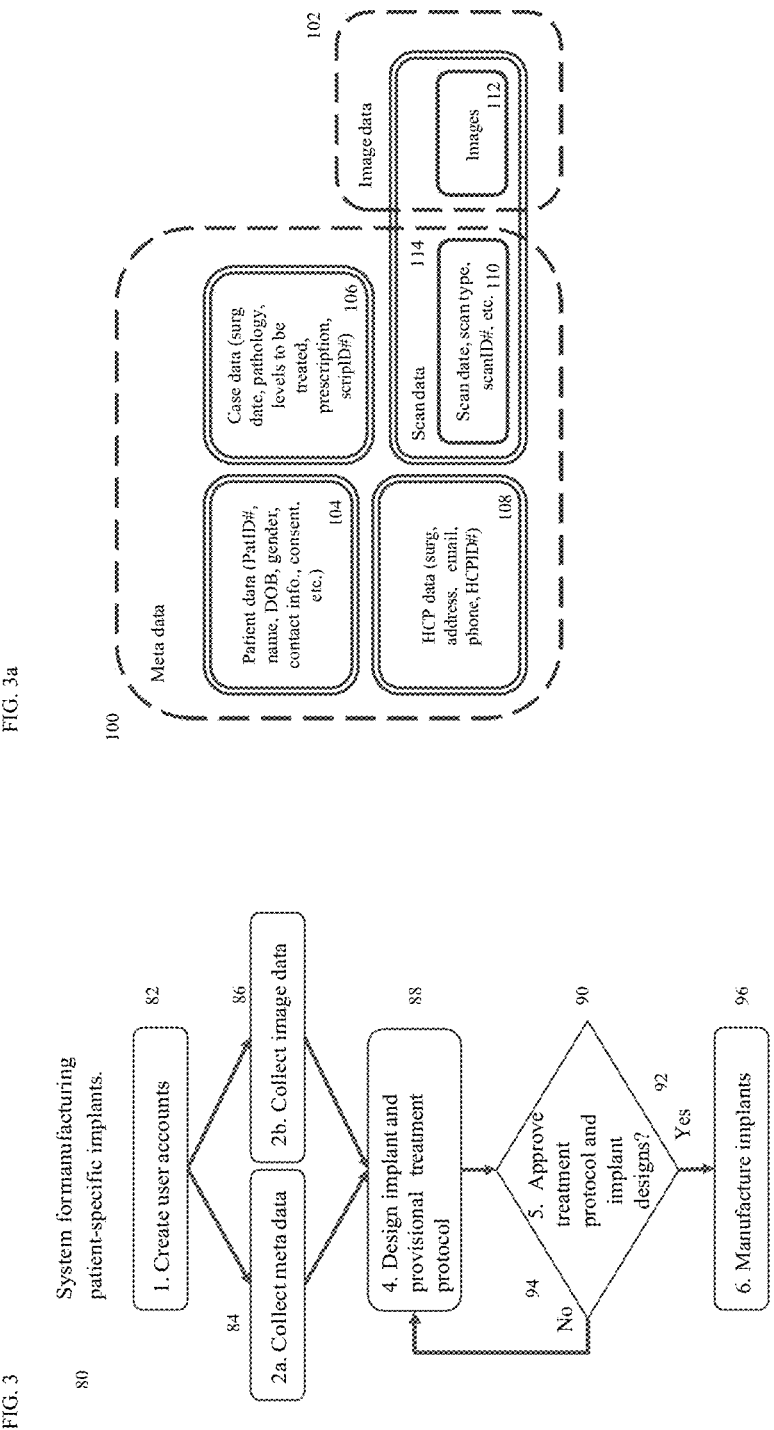

FIG. 5

CARLSMED
Patient Portal
STATUS

Surgery — Scheduled: XX/YY/ZZZZ
Implant shipping
Implant manufacture
Surgeon approval — Pending
Implant design — Complete: XX/YY/ZZZZ
Image upload — Complete: XX/YY/ZZZZ

FIG. 4

CARLSMED
Patient Portal

Patient Information

Patient ID#: [PatID#]
Patient name: [PatName]
Patient DOB: [PatDOB]
Patient gender: [PatGender]
Patient email: [PatEmail]

Consent

I hereby give my consent to use my personal information, including imaging data and information listed above, for the design of patient-specific implants.

Agreed and acknowledged. ☐

Upload Image Data

Image data location: [Path] [Browse] [Upload]

[Finish]

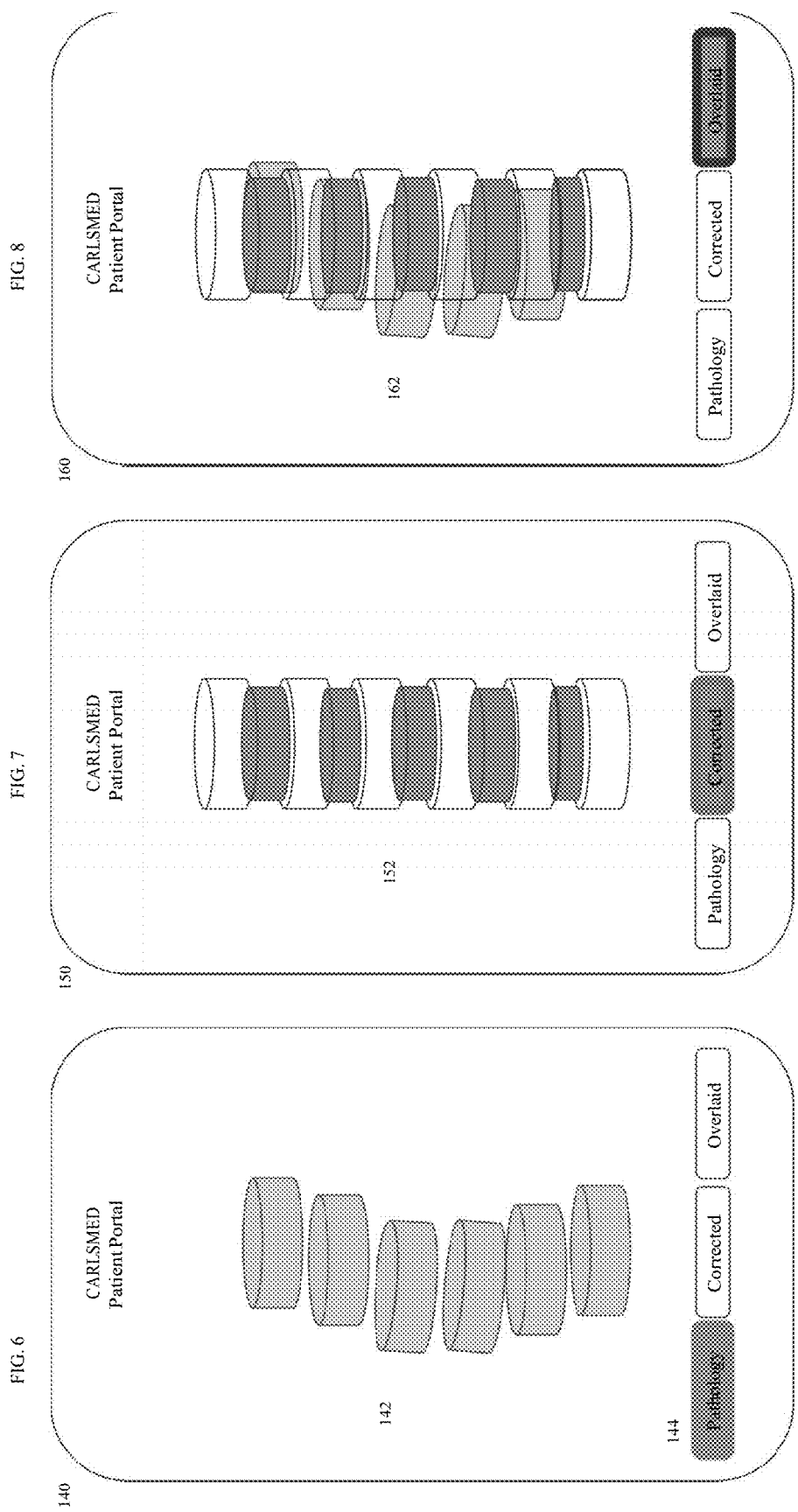

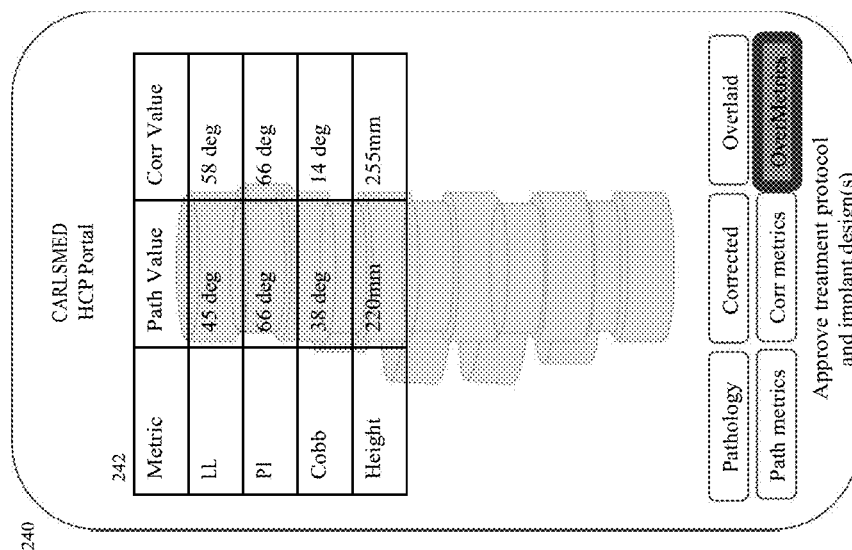
FIG. 14
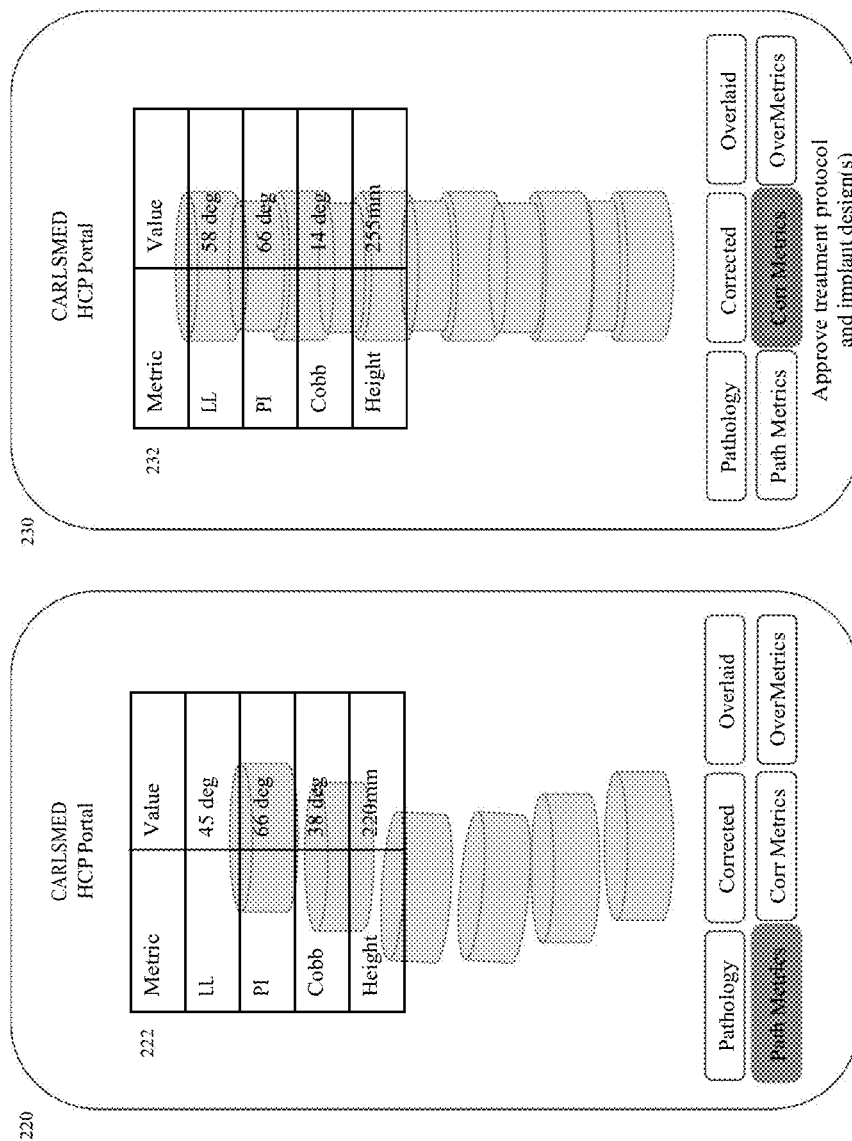
FIG. 15
FIG. 16

SYSTEMS AND METHODS FOR ORTHOPEDIC IMPLANTS

RELATED APPLICATION

This application is a continuation of U.S. patent application Ser. No. 16/699,447, filed Nov. 29, 2019 (now U.S. Pat. No. 12,133,803), which claims priority to U.S. Patent Application No. 62/773,127, filed Nov. 29, 2018, which are herein incorporated by reference in their entireties.

FIELD OF THE INVENTION

The field of the invention generally relates to orthopedic implants, including spinal implants, and methods for designing and producing them.

BACKGROUND

Orthopedic implants are used to correct a variety of different maladies. Orthopedic surgery utilizing orthopedic implants may include one of a number of specialties, including: spine surgery, hand surgery, shoulder and elbow surgery, total joint reconstruction (arthroplasty), skull reconstruction, pediatric orthopedics, foot and ankle surgery, musculoskeletal oncology, surgical sports medicine, and orthopedic trauma.

Orthopedic surgery may include joint replacement or other replacement of bony anatomical structures. In some instances, patients may require joint replacement due to degeneration of the joint or another disruption to the functional aspects of the joint. Additional orthopedic surgeries may include replacement of bones or sections of bone that have been compromised due to tumor or trauma. In one situation, a patient may require replacement of a section of a bone whose structural integrity has been compromised by a tumor. Additionally, resection of a tumor of the bone may be required as part of a treatment protocol to stem the propagation of cancer. In other instances, trauma, such as a motor vehicle accident or fall, may cause a severe fracture or disruption of bones. In these cases, sections of bones or entire bones may require replacement as part of the treatment protocol. Treatment protocol may include resection of anatomy, reorganization of anatomy, repair of anatomy, and delivery of therapeutic implants.

Spine surgery may encompass one or more of the cervical, thoracic, lumbar spine, the sacrum, or the pelvis and may treat a deformity or degeneration of the spine, or related back pain, leg pain, or other body pain. Irregular spinal curvature may include scoliosis, lordosis, and kyphosis (hyper- or hypo-). Irregular spinal displacement may include spondylolisthesis, lateral displacement, or axial displacement. Other spinal disorders include osteoarthritis, lumbar degenerative disc disease or cervical degenerative disc disease, lumbar spinal stenosis or cervical spinal stenosis.

Spinal fusion surgery may be performed to set and hold purposeful changes imparted on the spine during surgery. Spinal fusion procedures include PLIF (posterior lumbar interbody fusion), ALIF (anterior lumbar interbody fusion), TLIF (transverse or transforaminal lumbar interbody fusion), or LLIF (lateral lumbar interbody fusion), including DLIF (direct lateral lumbar interbody fusion) or XLIF (extreme lateral lumbar interbody fusion).

One goal of interbody fusion is to grow bone between vertebra in order to seize the spatial relationships in a position that provides enough room for neural elements, including exiting nerve roots. An interbody implant device (or interbody implant, interbody cage, or fusion cage, or spine cage) is a prosthesis used in spinal fusion procedures to maintain relative position of vertebra and establish appropriate foraminal height and decompression of exiting nerves. Each patient may have individual or unique disease characteristics, but most implant solutions include implants (e.g. interbody implants) having standard sizes or shapes (stock implants).

Software is often used throughout the orthopedic implant design process. Software can be used to view relevant anatomy and create specifications for orthopedic implants. Software can also be used to create, view, and modify three-dimensional virtual models representative of implants, anatomy, and other components. Additionally, software can be used to better understand spatial relationships between relevant anatomical elements.

BRIEF DESCRIPTION OF THE DRAWINGS

FIG. 3 shows a flow diagram describing one embodiment of a system for designing and manufacturing patient-specific implants.

FIG. 3a shows a diagram categorizing data for use in design of implants.

FIGS. 4 through 8 show several embodiments of views of displayable patient portal interfaces in accordance with various embodiments.

FIGS. 9 through 16 show several embodiments of views of displayable healthcare provider portal interfaces in accordance with various embodiments.

DETAILED DESCRIPTION

Figure 1:
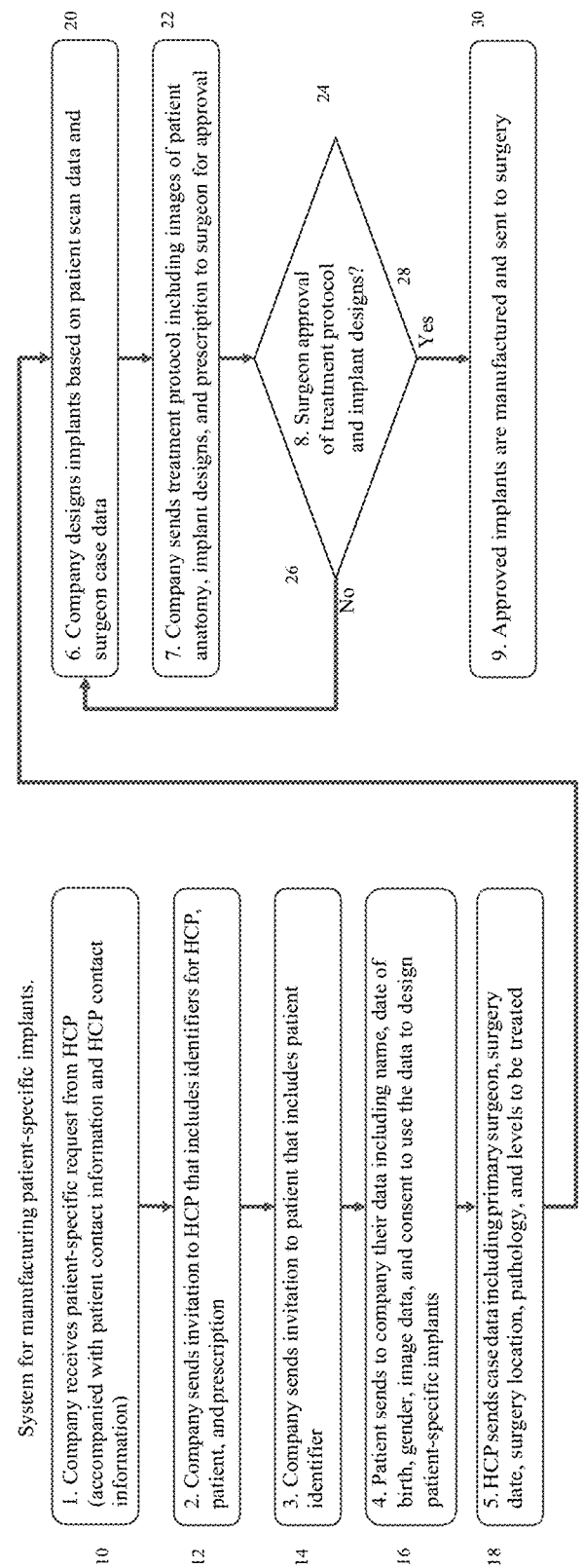
FIG. 1 shows a flowchart for designing a patient-specific orthopedic implant in accordance with one or more embodiments.

A patient-specific medical device and an efficient method of producing patient-specific orthopedic implants are described in the embodiments herein. Orthopedic implants and devices according to embodiments described herein may include spinal implants such as interbody implants, expandable implants, or fusion cages.

Orthopedic implants are typically intended to replace missing anatomy, correct pathological deformities, and/or restore anatomical relationships that have been compromised due to degeneration or aging. In some instances, implants can be used to replace anatomy that has been compromised due to fracture or trauma. In other instances, implants can be used to correct improper development. In other instances, implants can be used to restore relationships that have changed with the passing of time or advancement of a degenerative condition. Computing devices and software can be used throughout treatment, including imaging, diagnostics, planning, and/or design of corrective elements, including implants.

Software is typically used to view relevant internal anatomy, such as bones and soft tissue. When digital images (e.g., MRIs, CTs, or x-rays) of the patient's relevant anatomy are collected, they are displayed on computing systems that run image viewing software. The data from digital images can be saved in various formats to various media and transferred digitally through connected computers or networks of computers. Image data, as other digital data, can be sent through typical electronic networks by typical methods including email, file transfer protocol, and file sharing over servers. Software is further used to design implants, provide specifications for implants, and provide instructions for manufacture of orthopedic implants. The software can be CAD software or other software suitable for generating virtual models of anatomy, orthopedic implants, or the like.

Patient-specific implants can be designed for optimal fit in the negative space created by removal of anatomy and adjustment of the relative positions of bony anatomy. In spine surgery, surgical planning software can be used to virtually adjust the relative positions of vertebrae and define the space between the vertebrae. Modifying the spatial relationship between adjacent vertebrae within a virtual design space can provide a definition of the 3D space into which an interbody can be delivered. Software can further be used to compare the original pathological anatomy to a corrected anatomy. The optimal size and shape of patient-specific implants can prevent or reduce instances of implant failure.

One method of designing orthopedic implants includes the use of software designed to interface with patients, healthcare providers (HCP), and manufacturers. HCPs can be described as entities that provide care including, nurses, physicians, surgeons, clinicians, or others acting under the authority of the above.

One method of manufacturing orthopedic implants includes the use of additive manufacturing or three-dimensional printing (3DP). Additive manufacturing provides for manufacturing of complex components that could not otherwise be manufactured using traditional subtractive manufacturing (CNC machining, turning, milling, drilling, electron deposition manufacturing, broaching, rolling, stamping, etc.).

It is accepted that increasing engagement of the patient in medical treatment protocols increases the probability of improved outcomes. One method of increasing patient engagement is to encourage patient action prior to a surgical procedure. A patient who becomes personally engaged in pre-operative activities is more likely to be engaged in post-operative recovery activities, thereby improving the likelihood of improved outcomes.

A computing system can be configured to design patient-specific implants. The computing system can be configured to run software on multiple computing platforms and devices, such as desktop computers, laptop computers, tablet computes, hand-held computers, smart phones, or other devices.

The system can operate a series of steps arranged to collect and share information critical to the design and manufacture of orthopedic implants. In one embodiment, a manufacturer (company) receives a request from a surgeon for a patient-specific (e.g., custom, bespoke, personalized, matched, etc.) implant. The company then can send a request to the surgeon or qualified HCP soliciting information such as primary surgeon, digital imaging data (scan data), surgery date, treatment protocol, surgery location, patient pathology, location of pathology within patient, patient name, patient contact information, authority to contact patient directly, patient date of birth, and patient gender. A treatment protocol can be described by the surgeon or HCP and could include specific anatomy to remove, manipulate, or adjust and the implants to aid with surgical treatment of the patient's pathology. The collection of data outside of the digital imaging data can be described as meta data.

The company can contact the patient and request additional or missing information. The company can make direct requests of the patient to use their digital imaging data (or other relevant data) to design patient-specific implants. Company can implement data management and security measures to comply with Health Insurance Portability and Accountability Act including anonymizing patient data, removing electronic protected health information, and data encryption.

Digital imaging data can be acquired directly from the patient or from the HCP via electronic networks. Additionally, digital imaging data can be provided using electronic storage on portable media (such as flash drives or computer discs).

When the company has a complete file or nearly complete file with digital imaging data (e.g., scan data), patient data, HCP data, and case data, they can begin design of patient-specific implants. Following design of the patient-specific implants, the company can alert the HCP and/or patient and invite each to view the proposed treatment protocol.

Elements of a software solution can be referred to as portals or interfaces. Portals can be designed to interface with specific classes of users or clients such as (1) patients, (2) HCPs, and (3) manufacturers. Portals can be designed to display and collect information from a designated subset of users. A software solution can operate on a common set of data but only allow access to an appropriate subset of the data that coincides with each class of user. In one embodiment, a cloud-based data hub can be used to collect the common data. Cloud data storage is a model of computer data storage in which the data can be centrally stored on servers and remotely accessed. With proper permissions, multiple devices or users can gain access to the remotely stored data including smart phones, tablets, laptops, desktops, or other computing devices. The central location of the data provides for remote access for multiple users. Each user or class of user can have different abilities to use the data (read, write, download, etc.).

Portals and/or interfaces can refer to data structures and protocols for exchanging data with a remote user or computing device. In one embodiment, a portal includes a web application provided by a server computing device over a network such as the internet. A client computing device (e.g., a patient device, a physician device, an HCP device) may access to the portal provided by the computing device by using a network address, such as a URL (uniform resource locator). The server computing device can be configured to host the web application portal, including transmitting web pages to the client computing device. In some embodiments, a portal includes a set of web pages and/or web page templates generated by a server computing device. In some embodiments, a portal may include alternate methods of exchanging structured data with a client computing device. For example, a portal may include a server computing device in network communication with a client application at a remote computing device. A remote computing device can generally include a computing device in network communication with a computing system, such as a server computing device.

Interfaces can include predefined data structures and layouts. A server computing device may use interfaces to standardize data communication with client computing devices and/or end-users. In one embodiment, an interface includes a webpage with a graphical user interface. The server computing device may populate the interface with data from a database to generate a webpage. The interface may define how the data is to be displayed and define how users may interact with the data and computer system. For example, the interface may include HTML and ECMAScript (e.g., JavaScript) code for displaying a webpage at a client computing device. In another embodiment, the interface may include a software application implementing operating system libraries to provide an interactive user interface at a client computing device. A portal and/or interface may be configured to receive user input (e.g., user actions), including prompting/requesting user input, and receiving user input or user actions. For example, a webpage may include a text input field, and a file upload component.

In alternate embodiments, an interface includes a programmatic application data interface, commonly referred to as an API or application interface. The application interface defines data structures and protocols for network communication between a client and server computing device. An application interface may include a web API based on HTTP (hypertext transfer protocol). More specifically, a server computing device may receive HTTP requests over a network, and respond by retrieving/modifying data stored in a database and/or executing software routines at the server computing device (e.g., processing/transforming stored data, generating/capturing data). The application interface may include any suitable communication standard, such as a network file system protocol, database connectivity protocol, stateful request protocol, stateless request protocol, and so on.

One method of manufacturing orthopedic implants includes the use of software designed to interface with a patient via a patient portal. In one embodiment, a patient portal provides access to data that is germane to patients. A patient portal can create or display patient identifiers that are linked to the patient, surgery, and implants to be used in surgery. Using the patient identifier or an electronic link, the patient can gain access the patient portal. Additionally, the patient portal can be configured to collect, confirm or display other patient information (patient name, date of birth, gender, contact information, etc.). The patient portal can be constructed to receive image data directly from the patient via data input or upload. Another way of receiving information is to receive data from an external system, for instance, by communicating with hospital or office imaging systems, including PACS (Picture Archiving and Communication System). Furthermore, the patient portal can be constructed to receive consent from the patient relating to the use of image data in the design of the orthopedic implant. Additional useful features can include displaying of progress relating to delivery of the orthopedic implants.

One method of designing patient-specific interbody implants includes capturing important anatomical geometry and relative positioning using computed tomography (CT) or another imaging modality (MRI, simultaneous bi-planar radiography, etc.). The image data can be reconstructed into volumetric data containing voxels that are representative of anatomy.

One method of manufacturing orthopedic implants includes the use of software designed to interface with a physician or the office of the HCP, a HCP portal. In one embodiment, the physician has a unique identifier that can be linked to multiple patients under their care. Additionally, a physician may have an independent portal germane to their usage. Physicians and HCPs can have visibility to multiple patient data, workflows, and status to help provide improved patient care.

In one embodiment, the HCP portal allows a physician, nurse, physician assistant, nurse practitioner, or other party acting under the authority and direction of a HCP (such as office administrative staff) to gain access to relevant information. In one instance, a HCP portal can provide visibility to the designs of implants including, but not limited to, external envelope dimensional specifications (length, width, depth, coronal angle, sagittal angle, etc.), internal lattice specification, and implant stiffness. In one instance, an HCP portal can provide visibility to pathological anatomy, proposed correction plan and anatomy, anatomical metrics, and post-surgical image studies.

Furthermore, the HCP portal can provide an environment for granting approval of the treatment plan, including implant design. The portal can be used to collect, confirm or display information or solicit approval of treatments. The HCP portal can also be used by the physician to adjust or modify the prescription, treatment plan, or implant design based on their unique clinical appreciation of the pathological condition that requires surgery, or adjust or modify the proposed surgical plan. In one embodiment, physician approval of the treatment protocol or prescription, including the implant design, is required before manufacture and shipping from manufacturer. The HCP portal can provide an update of the workflow to help the HCP understand how the patient-specific implant is progressing through the design and manufacturing process.

One method of designing orthopedic implants includes the use of software designed to interface with the company, a company portal. The company portal can be configured to interface with design tools such as CAD software or imaging software. Design tools can be described as computer software used to design implants. Data can be extracted through the company portal and used with company software design tools to generate designs for implants. The implant designs can be returned to the data hub for display through the patient and HCP portals.

In one embodiment, the implant designs, treatment protocols, and resulting anatomical metrics can be displayed on the HCP portal for approval by the physician, surgeon, or authorized agent. After approval of the designs, protocols, and metrics, the company can manufacture the implant(s) to the specifications of the approved designs.

In some embodiments, a system generates the treatment protocol and manufactures the approved patient-specific implant. For example, a company can receive patient-specific request from HCP (accompanied with patient contact information and HCP contact information). The company can send an invitation to HCP that includes identifiers for HCP, patient, and prescription. The company may send an invitation to the patient that includes patient identifier at block 14. The patient may send to company their data including name, date of birth, gender, and image data. HCP sends case data including primary surgeon, surgery date, surgery location, pathology, and specific region(s) to be treated. The company can design implants based on patient scan data and/or surgeon case data. The company can send treatment protocol including images of patient anatomy, implant designs, and prescription to surgeon for approval. HCP may approve treatment protocol (plan) including implant designs. Approved implants are manufactured and sent to surgery.

FIG. 1 shows a flow chart for designing and manufacturing patient-specific implants in accordance with one or more embodiments. In general, a system can include a collection of data from various blocks 10, 12, 14, 16, 18, designing the orthopedic implants using the data collected at block 20, presenting a provisional treatment protocol and designs for physician approval at block 24, and manufacturing the implants at block 30. If the provisional treatment protocol and implant designs are not approved by the physician, the company can adjust the protocol and implant designs based on physician feedback at 26. If the provisional treatment protocol is approved at 28, the implant design specifications can be used for manufacturing. One method of manufacturing can include additive manufacturing using Titanium alloy, metals, rigid plastics, or the like. Details of the system are discussed below.

At block 10, the system for manufacturing can receive a patient-specific request from a HCP. The request can include, without limitation, patient contact information, healthcare contact provider information, user account information, authorization information, or combinations thereof.

At block 12, the system can send one or more identifiers for the HCP, patient, prescriptions, medical device, or the like to the HCP. In some embodiments, the identifiers can indicate account(s) for healthcare provider, a user account for the patient, or the like.

At block 14, the system can send an invitation to the patient. The invitation can include the patient identifier, login information, account information, or the like and, in some embodiments, can include instructions for setting up a user account and linking the user account to healthcare provider. The patient identifier can include, without limitation, one or more electronic links for setting up a user account, providing access to an account, etc.

At block 16, the patient can provide the system with data, including the patient's name, date of birth, gender, image data, and/or consent to use the data, or other data, such as data provided by the healthcare provider directly to the system. The patient can review data prior to approval and approve use of all the data or a subset of data. The patient data can be provided via email, an upload portal, FTP site, or the like. The HCP can send information or notifications to the patient to facilitate the patient's response to the invitation. In some embodiments, the HCP can send the invitation from the system directly to the patient via an SMS (Short Message Service), emails, etc. The patient can access the patient user account to manage data (including data sent from the patient, data sent from healthcare providers, or the like), settings (e.g., security settings), permissions, or the like. The user account can manage permissions for multiple healthcare providers, physicians, or individuals (e.g., family members) associated with the patient.

At block 18, the HCP can send data, including, without limitation, physician information (e.g., primary surgeon), procedure information (e.g., surgery date, surgery location, hospital information, etc.), pathology, treatment information (e.g., levels to be treated for spine surgeries), or the like. The data can be associated with the identified patient. In some embodiments, the data can include information from clinicians. The clinician information can include surgeon preferences, including preferred delivery instruments, preferred parameters for implants, or the like.

At block 20, the system can design one or more implants based on the patient data and/or surgeon case data. The surgeon case data can include symptom information, a diagnosis, and treatment information. The surgeon case data can be linked with the patient data.

At block 22, a treatment protocol can be sent to the healthcare provider for review, comment, and approval. The treatment protocol can include, without limitation, one or more images of the patient anatomy, implant designs, and prescription. The images of the patient anatomy can be annotated by the company to indicate implantation sites, surgical approaches, and anatomical features of interest, such as significant anatomical anomalies. This can assist with physician review. In some procedures, the treatment protocol can be sent to a hospital, which in turn distributes the treatment protocol to one or more members of a surgical team. The surgical team can review, revise, and approve, via healthcare portal, or the treatment protocol. In some embodiments, the system can generate post-treatment images illustrating the predicted post-treatment position of anatomical features. The physician can use the post-treatment images to assess the expected outcome and predict efficacy. The post-treatment images can be included in the treatment protocol or can be included in a post-treatment report.

At block 24, if the healthcare provider approves the treatment protocol and implant designs, the system can automatically begin the manufacturing process. In some embodiments, a surgeon can improve the treatment protocol and implant designs while also providing additional feedback that is incorporated into the implant design. For example, the surgeon can provide additional dimension/configuration, treatment input, or other information suitable for designing the implant. In some instances, the healthcare provider may acquire additional images the patient used in the approval process. The additional data can be sent to the company to update the design and/or treatment protocol.

If the surgeon rejects the proposed design and/or treatment protocol at 26, the surgeon can provide input for redesigning the implant. The system can update the implant design based on the input and can send the updated design and treatment protocols to the surgeon at block 22. This process can be repeated until the design and/or treatment protocol are approved.

Other embodiments may include instances where users (patients, physicians, HCP offices, etc.) do not need to provide the information using the software interface, but rather confirm the accuracy of collected data.

Figure 2:
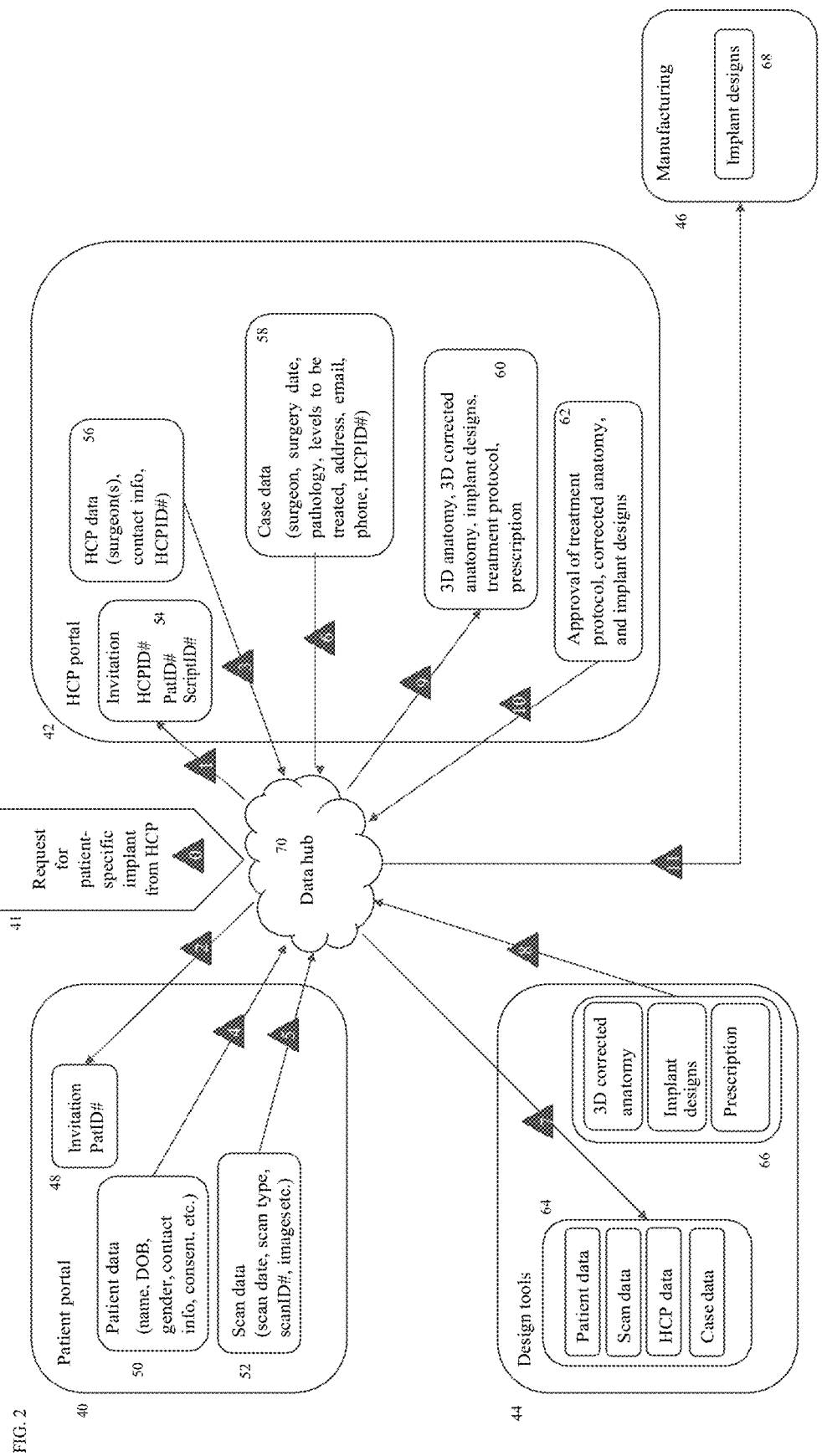
FIG. 2 shows a diagram describing information flow within a system for designing and manufacturing a patient-specific implant in accordance with one or more embodiments.

FIG. 2 shows a diagram describing information flow within a system for designing and manufacturing a patient-specific implant. The diagram is divided into portals 40, 42, 44 that are configured to facilitate information collection, exchange, and display based on the class of user. Additionally, a central database or data hub 70 ("data hub 70") can be configured to collect data and provide access to each user based on their class and permissions. A manufacturing section 46 represent a facility or machine configured to manufacture implants based on design specifications.

Each of the users are issued unique identifiers to allow for tracking of workflow, identification purposes, and traceability required for implantable devices. Other user information including names, date of birth, gender, and contact information may be helpful for data management purposes.

The process is initiated by a request for a patient-specific implant originating from the physician or HCP 41. After request 41 is received by the data hub, an invitation is sent to the HCP that includes issues or confirms a HCP identifier.

Patient portal 40 is configured to interface with the patient and facilitate collection or confirmation of patient-related data. In one embodiment, data hub 70 is configured to receive a request for a patient-specific orthopedic implant. Data hub 70 can be configured to send and receive data. Data hub 70 sends a message 54 to HCP via HCP portal 42 which confirms or assigns a HCP identifier (HCPID #), patient identifier (PatID #), and prescription identifier (ScriptID #). Data hub 70 sends a message to patient via patient portal 40 which confirms or assigns a patient identifier. If not already known, HCP sends data 56 to data hub 70 that may include affiliated surgeons. If not already known, patient sends patient data 50 to data hub 70. Patient sends scan data including images used for diagnostic purposes, date of image scan, type of image scan (typically in the DICOM image format), and patient consent to use such data in the design and manufacture of implants. Additionally, the patient may consent to use of their data for compiling within a database to aid with future treatments. Using HCP portal 42, HCP provides additional data 58 about the case including primary surgeon, surgery date, pathology, diagnosis, specific regions to be treated, and other information. After collection of all data 48, 50, 52, 54, 56, 58 within data hub 70, company can begin design of patient-specific implants. Using design tools 44, data collected via patient portal 40, and data collected via HCP portal 42, design of patient-specific implants can begin. Upon design of implants, including adjustment of anatomy from a pathological state to a corrected state, the provisional treatment protocol can be submitted through data hub 70 to the physician or HCP for approval within the HCP portal. Upon approval of treatment protocol 62, implant design specifications 68 are sent to manufacturing 46.

FIG. 3 shows a flow diagram 80 describing one embodiment of a system of designing and manufacturing patient-specific implants. In one embodiment, user accounts can be created 82 to provide a structure for data to be collected and linked. Typical users include patients and HCPs. System 80 can have multiple users based on the use of information within system 80. The HCP user group can be divided into different classes of users. For example, a surgeon may have different access and permissions than physician office personnel.

Following the creation of user accounts 82, collection of meta data 84 and collection image data 86 can begin. Meta data includes data that is used to describe other data, in this case, meta data represents data identifying patient, surgeon, case, and scan. Image data can be described as data representative of patient anatomy. In one scenario, image data can be collected as adjacent two-dimensional slices of cross-sectional anatomy. Consecutive two-dimensional cross-sectional images can be compiled into thee-dimensions to form a three-dimensional representation of anatomy.

After meta and image data are collected 84, 86 the data can be combined and used to design a provisional treatment protocol and associated implants 88. Following creation of a provisional treatment protocol and implant designs, a physician can be commissioned to provide approval of the protocol and implant designs. If protocol and designs are not in condition for approval 94, the surgeon can work with the company to devise an appropriate protocol and designs 88. Following approval, the implant designs are sent to manufacturing 96 and ultimately delivered to surgery for implantation into the patient.

FIG. 3a shows a diagram categorizing data to be used in the design and manufacture of patient-specific implants. This data is typically comprised of meta data 100 and image data 102. Meta data 100 can contain information such as patient identification 104 (name, contact information, date of birth, gender, acceptance of consent, etc.), HCP identification 108 (surgeon name, contact information, etc.), case data 106 (surgery date, pathology, diagnosis, treatment levels, etc.) and scan data 114 (scan date, scan type, DICOM data, images, etc.). Image data 102 can contain data related to the diagnostic images 112 of the patient obtained and collected by the HCP. Images 112 can be formatted as a three-dimensional collection of two-dimensional slices (typical to a CT or MRI volumetric scan). Scan data 110 can contain data identifying the scan date, scan type, scan settings, and DICOM data.

Figure 3B:
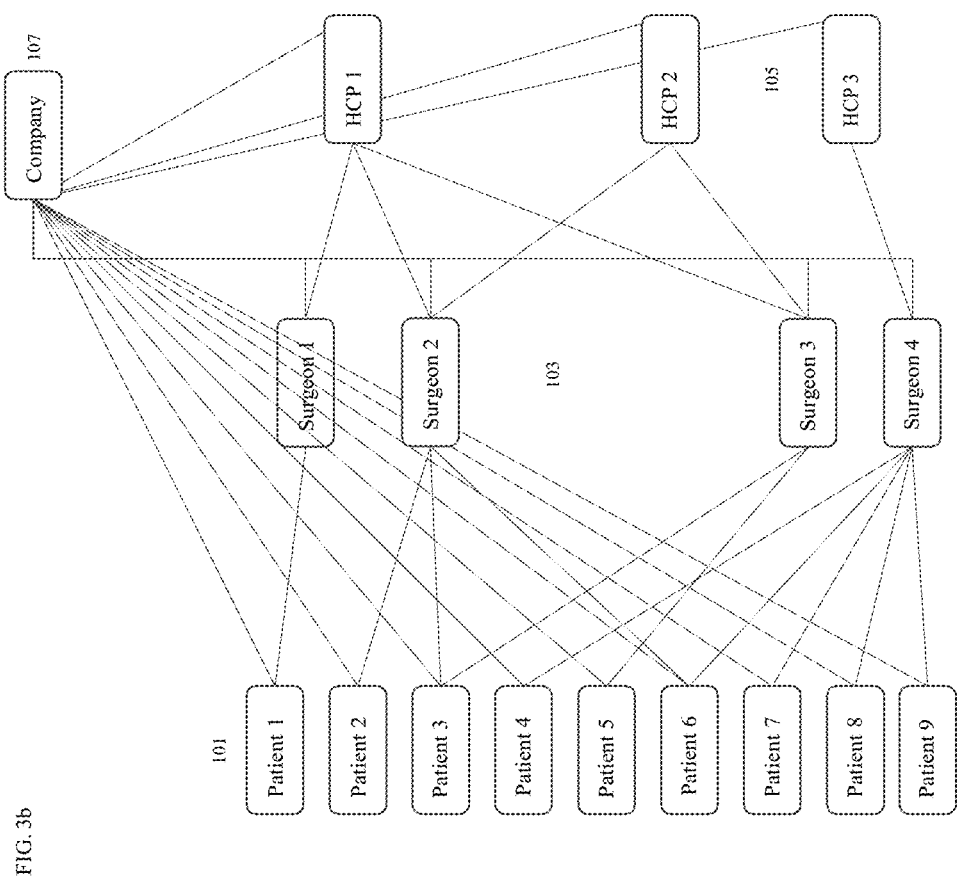
FIG. 3b shows a diagram showing relationships between users.

FIG. 3b shows a diagram showing relationships between users. The lines between users represent data that can be shared between users. In one embodiment, patients 101 are linked to one or more surgeons 103 and company 107. Surgeons 103 are linked to one or more patients 101, one or more HCP offices 105, and company 107. HCP offices 105 can be linked to one or more surgeons 103 and company 107. Company 107 is linked to all users; the company requires access to all of the information in order to design the surgical plan and deliver implants to surgery.

FIG. 4 shows one view of an embodiment of a patient portal interface 120. In this embodiment, the patient could be prompted to enter or confirm relevant information to aid with unique identification (patient identifier, name, date of birth, gender, email, etc.) 122. One further aspect of this interface is the consent section 124 asking for permission from the patient to use their data for design of the orthopedic implant. In another embodiment, patient consent can be granted to allow collection of anonymized demographic data and outcomes to help refine future treatment protocols. Another aspect of the interface provides for upload of digital imaging data 126.

FIG. 5 shows another view of a patient portal interface 130. In this view, a status graphic 132 is displayed to provide information to the patient regarding the status of the design, manufacture, and delivery of the orthopedic implant.

FIG. 6 shows another view of a patient portal interface 140. In this view, image(s) or a virtual model representing patient anatomy containing the pathological condition is displayed 142. The present image shows representations of a patient's spinal anatomy. The image(s) or models can be displayed and manipulated using typical touch-screen gestures including zoom, pan, and rotate. Virtual 'buttons' 144 below the image can be used to toggle between pathology captured by the pre-operative patient scan (pathological anatomy), corrected anatomy based on a treatment protocol, and a composite model showing both the pathological anatomy and the treatment protocol overlaid upon each other.

FIG. 7 shows another view of a patient portal interface 150. In this view, an image(s) or a virtual model representing corrected anatomy 152 as described by a treatment protocol is displayed.

FIG. 8 shows another view of a patient portal interface 160. In this embodiment, an image(s) or a virtual model representing a composite of both the pathological anatomy and the treatment protocol 162.

Each of the portals can be configured to provide different views and functionality for the different users or class of users. In the present embodiment, the views and functionalities within the patient portal shown in FIGS. 4 through 8 are different than the views of the HCP portal shown in FIGS. 9 through 16.

Figure 9:
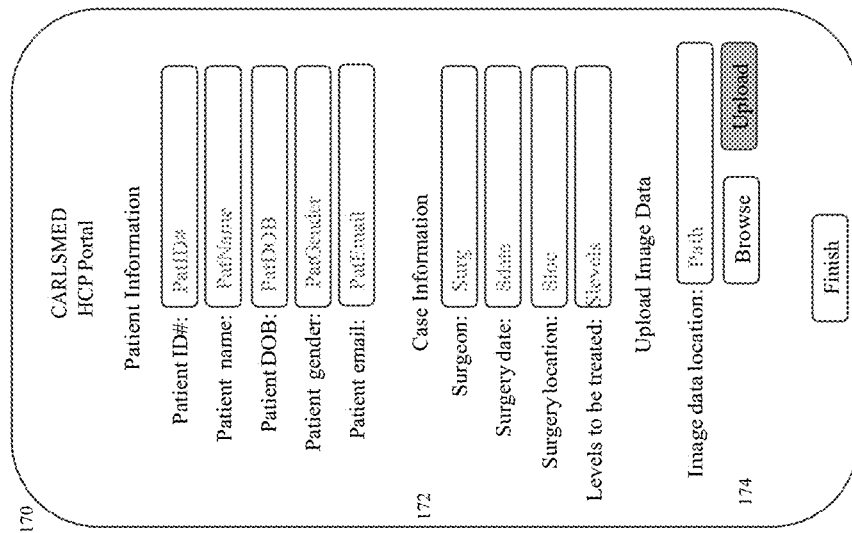

FIG. 9 shows one view of one embodiment of a HCP portal interface 170. In this embodiment, there is a section or sections 172 for a HCP to enter or confirm relevant information to aid with unique identification (patient identifier, patient name, patient date of birth, patient gender, patient email, primary surgeon, surgery date, surgery location, levels to be treated, etc.). Another section of the interface provides for upload of digital imaging data 174.

Figure 10:
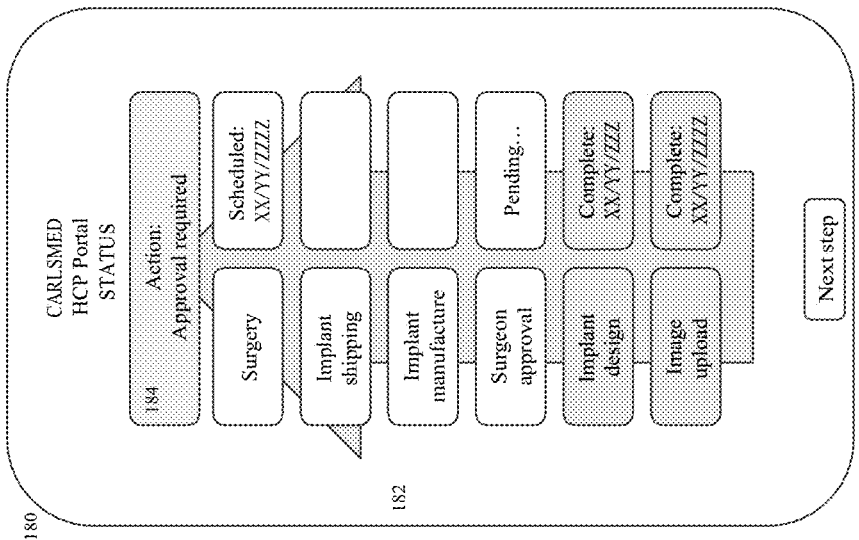

FIG. 10 shows another view of a HCP portal interface 180. In this view, a status interface 182 is displayed to provide information to the patient regarding the status of the design, manufacture, and delivery of the orthopedic implant. Presently, there is a notification regarding the status 184; in one instance, a HCP may be prompted by notification to review and approve treatment protocol as suggested. If approval is granted, the implant designs can move to manufacturing. If the protocol is not approved, suggested modifications from the surgeon can be incorporated, implants redesigned, and another notification sent to the HCP alerting them of pending approval of a different treatment protocol and implant designs.

Figure 11:
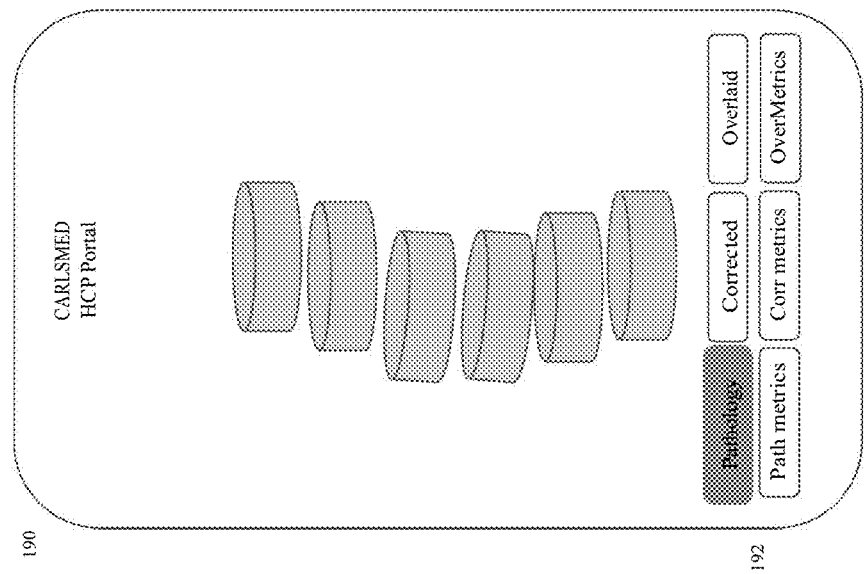
Figure 12:
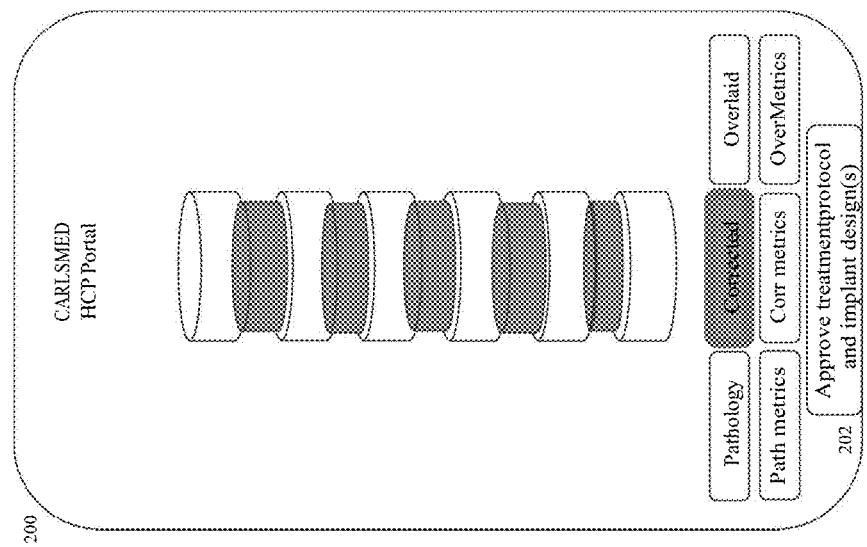
Figure 13:
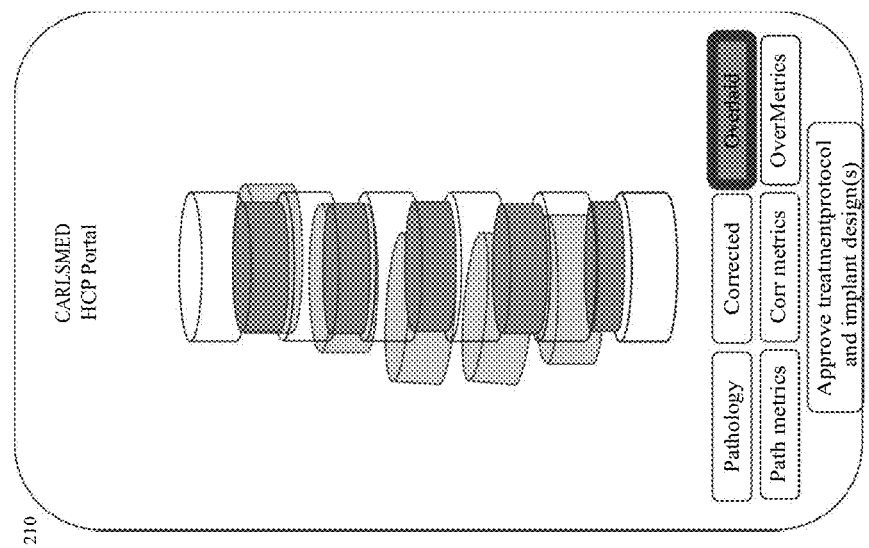

FIGS. 11 through 13 shows additional views of a HCP portal 190, 200, 210. In these views (as in FIGS. 6 through 8), image(s) or a virtual model representing patient anatomy is displayed. FIG. 11 shows representations of a patient's spinal anatomy containing the pathological condition, in this embodiment, a deformed spine. The image(s) or models can be displayed and manipulated using typical touch-screen gestures including zoom, pan, and rotate.

In these views of the HCP portal, section 192 contains several virtual 'buttons' that can be seen beneath the displayed anatomical model. Additional or different 'buttons' and the underlying functionality are present in different views and portals for different users; in the present embodiment, the 'buttons' for the HCP portal are different than those displayed on the patient portal (FIGS. 6 through 8). FIG. 12 displays a 'button' 202 that provides a physician the opportunity to approve the treatment protocol and implant designs.

FIG. 14 shows another view of an embodiment of a HCP portal interface. In view 220, table 222 displays relevant anatomical metrics typically used in the analysis and treatment of a spinal deformity. However, other metrics may be used to assess different orthopedic pathologies. In the present embodiment, lumbar lordosis (LL), pelvic incidence (PI), Cobb angle (Cobb), and height are displayed for the subject pathological anatomy.

FIG. 15 shows another view of an embodiment of a HCP portal interface. In view 230, table 232 displays the metrics representative of the corrected anatomy. The corrected anatomy is a result of the provisional treatment protocol.

FIG. 16 shows another view of an embodiment of a HCP portal interface. In view 240, table 242 allows for direct comparison of pathological and corrected metrics as a result of the provisional treatment protocol. These metrics are used by physicians to help assess the pathology and the provisional treatment protocol. The physician uses these metrics to help determine if the provisional treatment protocol can be approved to correct the pathology.

Figure 17:
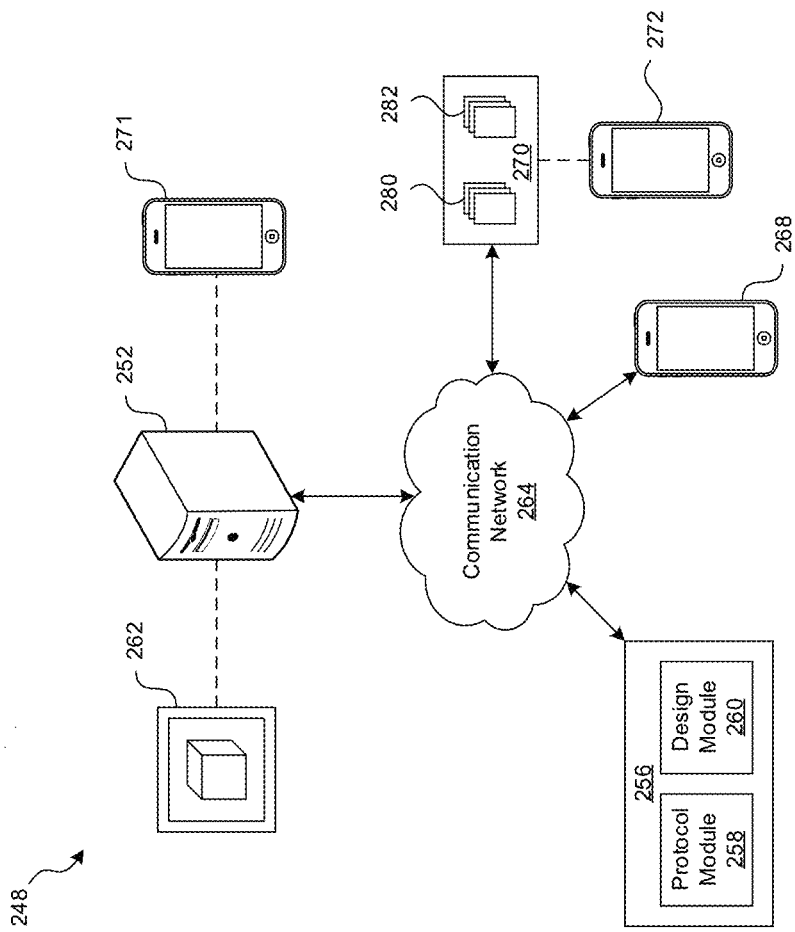
FIG. 17 illustrates a system for providing assistance for manufacturing patient specific-implants in accordance with one or more embodiments.

FIG. 17 illustrates a system 248 for manufacturing implants according to an embodiment. In some embodiments, a company system 252 can create a user account associated with a patient. Company system 252 may include a single server computing device, or multiple computing devices. The system 252 can also receive data from the patient device 268, a user device 272 (e.g., a computing device), and/or the healthcare provider 270. The system 248 can design a patient specific orthopedic implant based on the received data, and a manufacturing system 262 can produce the implant according to the design. The system 248 can also generate treatment protocols, which can include an entire surgical technique or portions thereof. The implant can be configured for the patient's anatomy as discussed in connection with FIGS. 1-16.

In robotic-assisted procedures, the robotic instructions from the system 248 can be used to control to a robotic apparatus (e.g., robotic surgery systems, navigation systems, etc.) for an implant surgery or by generating suggestions for medical device configurations to be used in surgery. In some procedures, both manual and robotic procedures can be performed. For example, one step of a surgical procedure can be manually performed by a surgeon and another step of the procedure can be performed by a robotic apparatus. Additionally, patient-specific components can be used with standard components made by the system 200. For example, in a spinal surgery, a pedicle screw kit can include both standard components and patient-specific customized components. For example, the implants (e.g., screws, screw holders, rods, etc.) can be designed and manufactured for the patient and the instruments can be standard instruments. This allows the components that are implanted to be designed and manufactured based on the patient's anatomy, and/or surgeon's preferences to enhance treatment. The patient-specific devices can improve, without limitation, delivery into the patient's body, placement at the treatment site, and interaction with the patient's anatomy.

The progress of treatment can be monitored over a period of time to help update the system 248. In trainable systems 248, post-treatment data can be used to train machine learning programs for developing surgical plans, patient-specific technology, or combinations thereof. Surgical plans can provide one or more characteristics of at least one medical device, surgical techniques, imaging techniques, etc.

With continued reference to FIG. 17, the system 248 may be connected to one or more communication networks 264. The communication network 264 may further be connected with a system 256, a patient device 268, and an HCP 270. The patient device 268 can send data to the system 252 via the network 264 and can provide access to patient portals. For example, the patient device 268 can display the patient portals discussed in connection with FIGS. 4-8. The HCP 270 can send patient data sets 280, 282 and provide access to HCP portals via a physician device 272. The communication network 264 may be a wired and/or a wireless network. The communication network 264, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and other communication techniques known in the art.

The system 256 may be implemented as a facility over "the cloud" and may include a group of modules. More specifically, system 256 may include a server computing device, or multiple computing devices in a distributed computing system. The group of modules may include a protocol module 258 and a design module 260. The system 256 can use one or more segmentation algorithms to process images. The segmentation algorithms can include, without limitation, one or more edge detection algorithms, boundary detection algorithms, thresholding, and other image processing algorithms and techniques applied to images. Anatomical elements or features in images (e.g., scans, digital images, etc.) can be identified after segmentation algorithms are used to segment features in images of the patient. The patient data can be imported into a modeling program to generate a CAD model of the patient's anatomy, including pre- and post-treatment models. The patient-specific CAD model can be used to generate an implant CAD model. A treatment CAD model can include both the patient-specific CAD model and the implant CAD model to allow for manipulation of the implant design, position of anatomical elements, or the like. The network 256 can convert the implant CAD model to manufacturing data.

The protocol module 258 can apply one or more algorithms to correct anatomy, develop implant designs, selected implant design, provide prescriptions, or the like. The protocol module 258 can serve as a data hub that collects information and store images of patients and types of implants, required in spinal surgeries. In some implementations, a similar module can be used for other types of surgeries to, for example, store patient data, device information, etc. The images stored by the protocol module 258 may be any of scans, camera images, Magnetic Resonance Imaging (MRI) images, ultrasound images, Computerized Aided Tomography (CAT) scan images, Positron Emission Tomography (PET) images, and X-Ray images. In one case, the images may be analyzed to identify anatomical features, abnormalities, and salient features in the images, for performing spinal surgeries on the patients. In some implementations, the protocol module 258 can store additional implant surgery information, such as patient information, (e.g., sex, age, height, weight, type of pathology, occupation, activity level, tissue information, health rating, etc.), specifics of implant systems (e.g., types and dimensions), availability of available implants, aspects of a surgeon's preoperative plan (e.g., surgeon's initial implant configuration, detection and measurement of the patient's anatomy on images, etc.), etc. In some implementations, the protocol module 258 can convert the implant surgery information into formats useable for implant suggestion models and algorithms. For example, the implant surgery information can be tagged with particular identifiers for formulas or can be converted into numerical representations suitable for supplying to a machine learning model. The protocol module 258 may include design tools. The designs tools can be used to measure distances between a number of salient features of one vertebra with salient features of another vertebra, for identifying implantation sites, spaces, disk pinches, bulges, etc. If the spinal abnormalities are identified, the protocol module 258 may graphically identify areas having the spinal abnormalities and may send such information to the HCP 270. The HCP 270 can respond to request for additional information.

The design module 260 can generate representations of anatomy, CAD models, manufacturing programs or instructions, segmentation tools, segmentation algorithms, etc. Output from the design module can be provided to the protocol module 258. The protocol module 258 and the design module 260 can work together to generate designs for implants and treatment protocols optimized for patient specific implant designs. In some embodiments, the design module 260 can generate one or more virtual models, tool paths, instruction sets, or the like for manufacturing. In some embodiments, the system 256 can form the methods discussed in connection with FIG. 1 and can include one or more systems discussed in connection with FIG. 18. For example, the protocol module 258 and the design module 260 can be components of the surgical assist system discussed in connection with FIG. 18.

The manufacturing system 262 can receive manufacturing data from the system 256. The manufacturing data can include virtual model data, tool path data, instruction sets, or the like. Additionally, the manufacturing system 262 can generate additional manufacturing data. The manufacturing system 262 can be a three-Dimensional (3D) printer. The 3D printer may be any general purpose 3D printer utilizing technologies such as Stereo-lithography (SLA), Digital Light Processing (DLP), Fused Deposition Modeling (FDM), Selective Laser Sintering (SLS), Selective laser melting (SLM), Electronic Beam Melting (EBM), Laminated object manufacturing (LOM) or the like. Other types of manufacturing devices can be used. The 3D printers can manufacture based on 3D fabrication data, which can be generated by the manufacturing system 262, system 256, or another computing device. The 3D fabrication data can include CAD data, 3D data, digital blueprints, stereolithography, or other data suitable for general purpose 3D printers. For example, the manufacturing system 262 can include a milling machine, a waterjet system, or combinations thereof, thereby providing manufacturing flexibility.

Manufacturing can be performed on site at the HCP 270 or off-site. On-site manufacturing can reduce the number of sessions with a patient and/or the time to be able to perform the surgery whereas off-site manufacturing can be useful to make the complex devices. In some embodiments, the manufacturing system 262 can be installed at the HCP 270. Off-site manufacturing facilities may have specialized manufacturing equipment. In some cases, complicated components of a surgical kit can be manufactured off-site while simpler components can be manufactured on site.

In one embodiment, information related to spinal surgeries may be displayed through a portal Graphical User Interface (GUI) of the user device 268, as illustrated using FIG. 17 a smart phone. Further, the user device 268, 272 may be any other device comprising a GUI, for example, a laptop, desktop, tablet, phablet, or other such devices known in the art. The device 268 can be used to access the patient portal (e.g., patient portal 40 of FIG. 2). The device 272 can be used to access the HCP portal (e.g., HCP portal 42 of FIG. 2) and used to approve or revise treatment protocols. The user devices 268, 272, and 271 may include client computing devices, patient computing devices, and physician computing devices.

Figure 18:
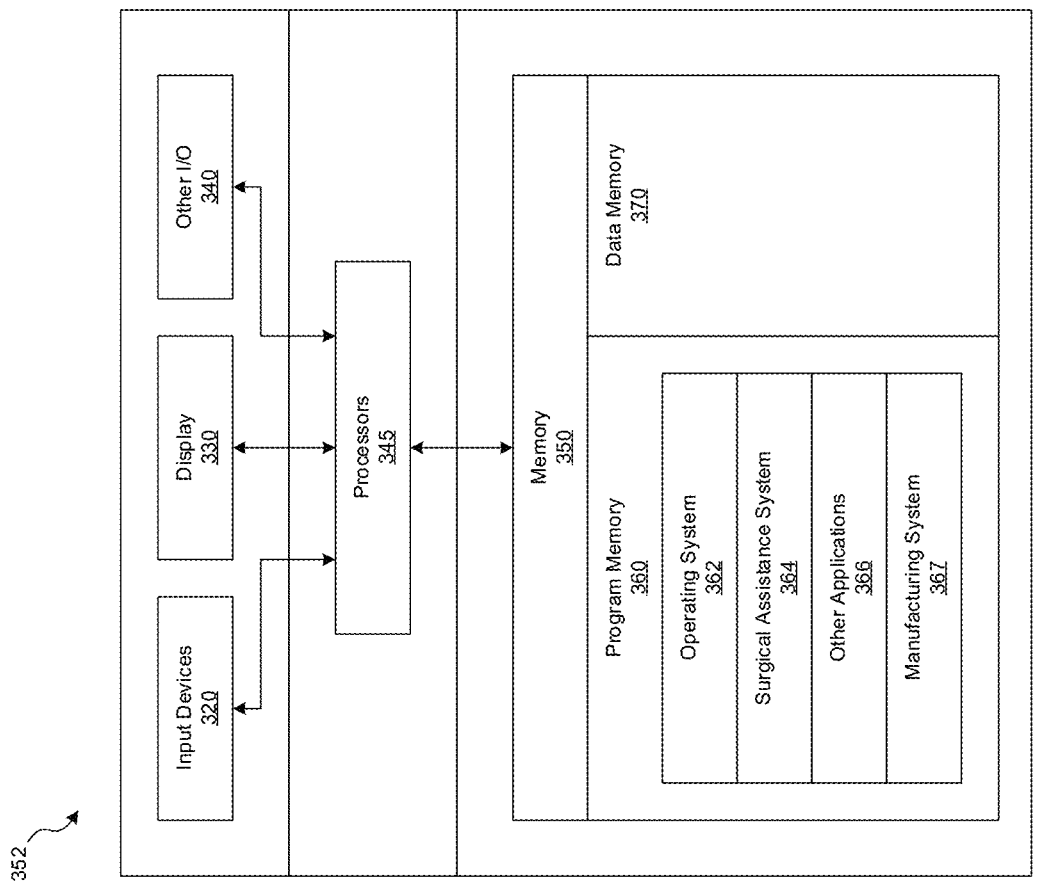
FIG. 18 illustrates a system for manufacturing patient specific-implants in accordance with one or more embodiments.

FIG. 18 illustrates a system 352 for manufacturing implants according to an embodiment. The system 352 can be part of the system 248 of FIG. 17. For example, the system 352 can be part of the system 252, design system 256, or another system or subsystem of the system 248 of FIG. 17. In some embodiments, the system 352 can obtain implant surgery information (e.g., digital data, images of anatomy, correction procedure data, HCP data, case data, etc.), convert the implant surgery information into a form compatible with an analysis procedure, apply the analysis procedure to obtain results, and use the results to manufacture the patient-specific implant. The system 352 can be in communication with a data hub (e.g., data hub 70 of FIG. 2) and can provide a patient portal interface, manage manufacturing of the patient-specific implants, receive meta data, and other functions. Multiple systems 352 can communicate with one another via a wired or wireless connection. In some embodiments, the surgical assistance system 364 can be used to create user accounts, collect patient data, collect imaging data, and design an implant from patient data imaging data. The I/O devices 340 can provide access to portals, inputting information to create user accounts, etc. A display 330 can display the collected patient data. Memory 350 can serve as a data hub and can store the patient data, imaging data, and other data.

The system 352 can handle the entire design and manufacturing process. In other embodiments, a physician can alter the implant configuration for further customization. An iterative design process can be employed in which the physician and system 352 work together, as discussed in connection with FIG. 1. For example, the system 352 can generate a proposed patient-specific implant. The physician can identify characteristics of the implant to be changed and can input potential design changes. For example, the physician can use a computing device (e.g., device 272 of FIG. 17) to view the implant design and then provide input for changing the design. The system 352 can analyze the feedback from the physician to determine a refined patient-specific implant design and to produce a patient-specific model. This process can be repeated any number of times until arriving at a suitable design. Once approved, the implant can be manufactured based on the selected design.

The system 352 can include a surgical assistance system 364. In some embodiments, the surgical assistant 364 can include one or more protocol modules, design modules, or other modules discussed in connection with FIG. 17. The surgical assistant system 364 can analyze implant surgery information, for example, into arrays of integers or histograms, segments images of anatomy, manipulates relationships between anatomic elements, converts patient information into feature vectors, or extracts values from the pre-operative plan. The system 352 can store implant surgery information analyzed by the surgical assistance system 364. The stored information can include received images of a target area, such as MRI scans of a spine, digital images, X-rays, patient information (e.g., sex, weight, etc.), virtual models of the target area, a database of technology models (e.g., CAD models), and/or a surgeon's pre-operative plan.

In some implementations, surgical assistance system 364 can analyze patient data to identify or develop a corrective procedure, identify anatomical features, etc. The anatomical features can include, without limitation, vertebra, vertebral discs, bony structures, or the like. The surgical assistance system 364 can determine the implant configuration based upon, for example, a corrective virtual model of the subject's spine, risk factors, surgical information (e.g., delivery paths, delivery instruments, etc.), or combinations thereof. In some implementations, the physician can provide the risk factors before or during the procedure. Patient information can include, without limitation, patient sex, age, bone density, health rating, or the like.

In some implementations, the surgical assistance system 364 can apply analysis procedures by supplying implant surgery information to a machine learning model trained to select implant configurations. For example, a neural network model can be trained to select implant configurations for a spinal surgery. The neural network can be trained with training items each comprising a set of images (e.g., camera images, still images, scans, MRI scans, CT scans, X-ray images, laser-scans, etc.) and patient information, an implant configuration used in the surgery, and/or a scored surgery outcome resulting from one or more of: surgeon feedback, patient recovery level, recovery time, results after a set number of years, etc. This neural network can receive the converted surgery information and provide output indicating the implant configuration.

The assistance system 364 can generate one or more virtual models (e.g., 2D models, 3D models, CAD models, etc.) for designing and manufacturing items. For example, the surgical assistance system 364 can build a virtual model of a surgery target area suitable for manufacturing surgical items, including implants. The surgical assistance system 364 can also generate implant manufacturing information, or data for generating manufacturing information, based on the computed implant configuration. The models can represent the patient's anatomy, implants, candidate implants, etc. The model can be used to (1) evaluate locations (e.g., map a negative 2D or 3D space), (2) select a bounding anatomical feature, such as a vertebral endplate, (3) create a best-fit virtual implant, (4) define a perimeter of the anatomical feature, and/or (5) extrude a volume defined by the perimeter and perpendicular to, for example, a best-fit plane to the interface of another anatomical feature. Anatomical features in the model can be manipulated according to a corrective procedure. Implants, instruments, and surgical plans can be developed based on the pre or post-manipulated model. Neural networks can be trained to generate and/or modify models, as well as other data, including manufacturing information (e.g., data, algorithms, etc.).

In another example, the surgical assistance system 364 can apply the analysis procedure by performing a finite element analysis on a generated three-dimensional model to assess, for example, stresses, strains, deformation characteristics (e.g., load deformation characteristics), fracture characteristics (e.g., fracture toughness), fatigue life, etc. The surgical assistance system 364 can generate a three-dimensional mesh to analyze the model. Machine learning techniques to create an optimized mesh based on a dataset of vertebrae, bones, implants, tissue sites, or other devices. After performing the analysis, the results could be used to refine the selection of implants, implant components, implant type, implantation site, etc.

The surgical assistance system 364 can perform a finite element analysis on a generated three-dimensional model (e.g., models of the spine, vertebrae, implants, etc.) to assess stresses, strains, deformation characteristics (e.g., load deformation characteristics), fracture characteristics (e.g., fracture toughness), fatigue life, etc. The surgical assistance system 364 can generate a three-dimensional mesh to analyze the model of the implant. Based on these results, the configuration of the implant can be varied based on one or more design criteria (e.g., maximum allowable stresses, fatigue life, etc.). Multiple models can be produced and analyzed to compare different types of implants, which can aid in the selection of a particular implant configuration.

The surgical assistance system 364 can incorporate results from the analysis procedure in suggestions. For example, the results can be used to suggest a treatment protocol or plan (e.g., a PLIF plan, a TLIF plan, a LLIF plan, a ALIF plan, etc.), select and configure an implant for a procedure, annotate an image with suggested insertions points and angles, generate a virtual reality or augmented reality representation (including the suggested implant configurations), provide warnings or other feedback to surgeons during a procedure, automatically order the necessary implants, generate surgical technique information (e.g., insertion forces/torques, imaging techniques, delivery instrument information, or the like), etc. The suggestions can be specific to implants. In some procedures, the surgical assistance system 364 can also be configured to provide suggestions for conventional implants. In other procedures, the surgical assistance system 364 can be programmed to provide suggestions for patient-specific or customized implants. The suggestion for the conventional implants may be significantly different from suggestions for patient-specific or customized implants.

The system 352 can simulate procedures using a virtual reality system or modeling system. One or more design parameters (e.g., dimensions, implant configuration, instrument, guides, etc.) can be adjusted based, at least in part, on the simulation. Further simulations (e.g., simulations of different corrective procedures) can be performed for further refining implants. In some embodiments, design changes are made interactively with the simulation and the simulated behavior of the device based on those changes. The design changes can include material properties, dimensions, or the like.

The surgical assistance system 364 can improve efficiency, precision, and/or efficacy of implant surgeries by providing more optimal implant configuration, surgical guidance, customized surgical kits (e.g., on-demand kits), etc. This can reduce operational risks and costs produced by surgical complications, reduce the resources required for preoperative planning efforts, and reduce the need for extensive implant variety to be prepared prior to an implant surgery. The surgical assistance system 364 provides increased precision and efficiency for patients and surgeons.

In orthopedic surgeries, the surgical assistance system 364 can select or recommend implants, surgical techniques, patient treatment plans, or the like. In spinal surgeries, the surgical assistance system 364 can select interbody implants, pedicle screws, and/or surgical techniques to make surgeons more efficient and precise, as compared to existing surgical kits and procedures. The surgical assistance system 364 can also improve surgical robotics/navigation systems, and provide improved intelligence for selecting implant application parameters. For example, the surgical assistance system 364 empowers surgical robots and navigation systems for spinal surgeries to increase procedure efficiency and reduce surgery duration by providing information on types and sizes, along with expected insertion angles. In addition, hospitals benefit from reduced surgery durations and reduced costs of purchasing, shipping, and storing alternative implant options. Medical imaging and viewing technologies can integrate with the surgical assistance system 364, thereby providing more intelligent and intuitive results. The healthcare provider can provide feedback about the output from the surgical assistance system 364. The surgical assistance system 354 can use the feedback to adjust treatment protocols, implant designs (e.g., configurations, materials, etc.), etc.

The system 352 can include one or more input devices 320 that provide input to the processor(s) 345 (e.g., CPU(s), GPU(s), HPU(s), etc.), notifying it of actions. The input devices 320 can be used to manipulate a model of the spine. The actions can be mediated by a hardware controller that interprets the signals received from the input device and communicates the information to the processors 345 using a communication protocol. Input devices 320 include, for example, a mouse, a keyboard, a touchscreen, an infrared sensor, a touchpad, a wearable input device, a camera- or image-based input device, a microphone, or other input devices (e.g., devices 268 and 272 of FIG. 17). Processors 345 can be a single processing unit or multiple processing units in a device or distributed across multiple devices. Processors 345 can be coupled to other hardware devices, for example, with the use of a bus, such as a PCI bus or SCSI bus.

The system 352 can include a display 330 used to display text, models, virtual procedures, surgical plans, implants, and graphics. In some implementations, display 330 can display the patient portal, HCP portal, or other portals or interfaces. The image(s) or models can be displayed and manipulated using typical touch-screen gestures via the display 330 (e.g., when the display 330 is part of the devices 268 and/or 272 of FIG. 17), including zoom, pan, and rotate.

In other embodiments, the I/O device 340 is used to zoom, pan, rotate, or otherwise manipulate the images. In some implementations, display 330 provides graphical and textual visual feedback to a user. In some implementations, display 330 includes the input device as part of the display, such as when the input device is a touchscreen or is equipped with an eye direction monitoring system. The processors 345 can communicate with a hardware controller for devices, such as for a display 330. In some implementations, the display is separate from the input device. Examples of display devices are: an LCD display screen, an LED display screen, a projected, holographic, or augmented reality display (such as a heads-up display device or a head-mounted device), and so on. Other I/O devices 340 can also be coupled to the processors 345, such as a network card, video card, audio card, USB, firewire or other external device, camera, printer, speakers, CD-ROM drive, DVD drive, disk drive, or Blu-Ray device. Other I/O 340 can also include input ports for information from directly connected medical equipment such as imaging apparatuses, including MRI machines, X-Ray machines, CT machines, etc. Other I/O 340 can further include input ports for receiving data from these types of machine from other sources, such as across a network or from previously captured data, for example, stored in a database.

In some implementations, the system 352 also includes a communication device capable of communicating wirelessly or wire-based with a network node. The communication device can communicate with another device or a server through a network using, for example, TCP/IP protocols. System 352 can utilize the communication device to distribute operations across multiple network devices, including imaging equipment, manufacturing equipment, etc.

The system 352 can include memory 350. The processors 345 can have access to the memory 350, which can be in a device or distributed across multiple devices. Memory 350 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 350 can include program memory 360 that stores programs and software, such as an operating system 362, surgical assistance system 364, and other application programs 366, such as program for managing a data hub. Memory 350 can also include data memory 370 that can include, e.g., patients data (name, DOB, gender, contact information, consent, scan data, etc.), implant information, configuration data, settings, user options or preferences, etc., which can be provided to the program memory 360 or any element of the system 352, such as a manufacturing system 367. The description of the manufacturing system 262 of FIG. 17 applies equally to the manufacturing system 367 of FIG. 18

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2017, titled "SYSTEMS AND METHODS FOR ASSISTING AND AUGMENTING SURGICAL PROCEDURES;"

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"

U.S. application Ser. No. 16/207,116, filed on Dec. 1, 2018, titled "SYSTEMS AND METHODS FOR MULTI-PLANAR ORTHOPEDIC ALIGNMENT;"

U.S. application Ser. No. 16/383,215, filed on Apr. 12, 2019, titled "SYSTEMS AND METHODS FOR ORTHOPEDIC IMPLANT FIXATION;" and U.S. Application No. 62/773,127, filed on Nov. 29, 2018, titled "SYSTEMS AND METHODS FOR ORTHOPEDIC IMPLANTS."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

While embodiments have been shown and described, various modifications may be made without departing from the scope of the inventive concepts disclosed herein.

What is claimed is:

1. A computer-implemented method comprising:
    providing access, via at least one user device portal of an implant design system, to an interactive graphical user interface (GUI) having a viewable image of a virtual model of a spine of a patient, one or more user inputs for selecting display of at least one of a plurality of pre-operative metrics or a plurality of post-operative metrics associated with the virtual model,
        wherein the at least one user device portal is linked to case data such that the interactive GUI provides access to at least a portion of the case data;
        wherein the implant design system is configured to be used to generate, at least partially using at least one trained machine learning model, a treatment plan that includes
            a pre-operative pathology of the patient, and
            a planned corrected anatomy of the patient after installation of a patient-specific implant;
    receiving, via a user-selectable element of the interactive GUI, approval of the treatment plan;
    after the patient-specific implant designed by the implant design system is implanted in the patient, receiving, via the at least one user device portal, one or more post-operative images of the patient;
    displaying, via the at least one user device portal, a post-operative review interface including
        a pre-operative pathology image and associated pre-operative metrics of the patient, and
        a planned corrected anatomical image and associated planned corrected metrics of the patient, wherein the planned corrected anatomical image shows the virtual model of the spine, in a corrected position, with a representation of the patient-specific implant; and
    retraining the at least one trained machine learning model using at least a portion of the received one or more post-operative images indicative of an outcome of the treatment plan, wherein the at least one retrained machine learning model is configured to receive new patient data for another patient and to generate a new treatment plan for the another patient based on the new patient data.

2. The computer-implemented method of claim 1, further comprising:
    linking the at least one user device portal to a patient identifier, a surgery, and the patient-specific implant for the surgery; and
    linking the at least one user device portal to multiple patients for viewing multiple patient data.

3. The computer-implemented method of claim 1, wherein the interactive GUI includes a window that concurrently displays an image of a pre-operative pathology of the patient and an image of a post-operative anatomy of the patient for visual comparison by a user associated with the at least one user device portal, wherein the one or more user inputs includes a first button for selecting display of the plurality of pre-operative metrics and a second button for selecting display of the plurality of post-operative metrics associated with the virtual model.

4. The computer-implemented method of claim 1, wherein the at least one user device portal includes:
    a patient portal for receiving first data from the patient to be added to the case data; and
    a healthcare portal for receiving second data from a healthcare provider to be added to the case data.

5. The computer-implemented method of claim 1, wherein retraining of the at least one trained machine learning model is based on a similarity score between a modeled result for the treatment plan and an actual post-operative result of the patient.

6. The computer-implemented method of claim 1, wherein the patient-specific implant is a cage, a rod, a plate, or a spinal fusion device.

7. The computer-implemented method of claim 1, wherein the planned corrected anatomical image includes an image of a virtual model representing an anatomy of the patient in a corrected configuration and annotation for the patient-specific implant.

8. The computer-implemented method of claim 1, wherein the viewable image of the virtual model includes at least one of a first image representing pre-operative pathology of the patient or a second image representing a corrected anatomy of the patient.

9. The computer-implemented method of claim 1, further comprising:
    receiving post-operative data including at least one of a set of post-operative images of the patient, physician feedback, patient recovery level, recovery time, or result after a period of time; and
    comparing at least a portion of the post-operative data to the treatment plan, wherein selection of the portion of the received post-operative data as one or more training items is based on the comparison, wherein the one or more training items are inputted into the at least one trained machine learning model for the retraining.

10. The computer-implemented method of claim 1, further comprising:
    receiving post-operative data of the patient; and
    determining spinal metrics for comparing a pre-operative pathology of the patient, a planned correction of the patient, and a post-operative anatomy of the patient, wherein the post-operative anatomy is based on the post-operative data.

11. The computer-implemented method of claim 1, wherein displaying the pre-operative metrics and the planned corrected metrics includes concurrently displaying the pre-operative metrics in a first column and the planned corrected metrics in a second column.

12. The computer-implemented method of claim 11, wherein corresponding metrics of the pre-operative metrics and the planned corrected metrics are aligned horizontally.

13. A system comprising:
one or more processors; and
one or more memories storing instructions that, when executed by the one or more processors, cause the system to perform a process comprising:
providing access, via at least one user device portal of an implant design system, to an interactive graphical user interface (GUI) having a viewable image of a virtual model of a spine of a patient, and one or more user inputs for selecting display of at least one of a plurality of pre-operative metrics or a plurality of post-operative metrics associated with the virtual model,
wherein the at least one user device portal is linked to case data such that the interactive GUI provides access to at least a portion of the case data;
wherein the implant design system is configured to be used to generate, at least partially using at least one trained machine learning model, a treatment plan that includes
a pre-operative pathology of the patient, and
a planned corrected anatomy of the patient after installation of a patient-specific implant;
receiving, via a user-selectable element of the interactive GUI, approval of the treatment plan;
after the patient-specific implant designed by the implant design system is implanted in the patient, receiving, via the at least one user device portal, one or more post-operative images of the patient; and
displaying, via the at least one user device portal, a post-operative review interface including
a pre-operative pathology image and associated pre-operative metrics of the patient, and
a planned corrected anatomical image and associated planned corrected metrics of the patient, wherein the planned corrected anatomical image shows the virtual model of the spine, in a corrected position, with a representation of the patient-specific implant,
retraining the at least one trained machine learning model using at least a portion of the received one or more post-operative images indicative of an outcome of the treatment plan, wherein the at least one retrained machine learning model is configured to receive new patient data for another patient and to generate a new treatment plan for the another patient based on the new patient data.

14. The system of claim 13, wherein the process further comprises:
linking the at least one user device portal to a patient identifier, a surgery, and the patient-specific implant for the surgery; and
linking the at least one user device portal to multiple patients for viewing multiple patient data.

15. The system of claim 13, wherein the interactive GUI includes a window that concurrently displays an image of a pre-operative pathology of the patient and an image of a post-operative anatomy of the patient for visual comparison by a user associated with the at least one user device portal.

16. The system of claim 13, wherein the at least one user device portal includes:
a patient portal for receiving first data from the patient to be added to the case data; and
a healthcare portal for receiving second data from a healthcare provider to be added to the case data.

17. The system of claim 13, wherein retraining of the at least one trained machine learning model is based on a similarity score between a modeled result for the treatment plan and an actual post-operative result of the patient.

18. The system of claim 13, wherein the patient-specific implant is a cage, a rod, a plate, or a spinal fusion device.

19. The system of claim 13, wherein the planned corrected anatomical image includes an image of a virtual model representing an anatomy of the patient in a corrected configuration and annotation for the patient-specific implant.

20. The system of claim 13, wherein the viewable image of the virtual model includes at least one of a first image representing pre-operative pathology of the patient or a second image representing a corrected anatomy of the patient.

21. The system of claim 13, wherein the process further comprises:
receiving post-operative data including at least one of a set of post-operative images of the patient, physician feedback, patient recovery level, recovery time, or result after a period of time; and
comparing at least a portion of the post-operative data to the treatment plan, wherein selection of the portion of the received post-operative data as one or more training items is based on the comparison, wherein the one or more training items are inputted into the at least one trained machine learning model for the retraining.

22. The system of claim 13, wherein the process further comprises:
receiving post-operative data of the patient; and
determining spinal metrics for comparing a pre-operative pathology of the patient, a planned anatomy of the patient, and a post-operative anatomy of the patient, wherein the post-operative anatomy is based on the post-operative data.

23. A non-transitory computer-readable medium storing instructions that, when executed by a computing system, cause the computing system to perform operations comprising:
providing access, via at least one user device portal of an implant design system, to an interactive graphical user interface (GUI) having a viewable image of a virtual model of a spine of a patient, and one or more user inputs for selecting display of at least one of a plurality of pre-operative metrics or a plurality of post-operative metrics associated with the virtual model,
wherein the at least one user device portal is linked to case data such that the interactive GUI provides access to at least a portion of the case data;
wherein the implant design system is configured to be used to generate, at least partially using at least one trained machine learning model, a treatment plan that includes
a pre-operative pathology of the patient, and
a planned corrected anatomy of the patient after installation of a patient-specific implant;
receiving, via a user-selectable element the interactive GUI, approval of the treatment plan;
after the patient-specific implant designed by the implant design system is implanted in the patient, receiving, via the at least one user device portal, one or more post-operative images of the patient;
displaying, via the at least one user device portal, a post-operative review interface including
a pre-operative pathology image and associated pre-operative metrics of the patient, and
a planned corrected anatomy image and associated planned corrected metrics of the patient, wherein the planned corrected anatomy image shows the virtual model of the spine, in a corrected position, with a
representation of the patient-specific implant; and
retraining the at least one trained machine learning model using at least a portion of the received one or more post-operative images indicative of an outcome of the treatment plan, wherein the at least one retrained machine learning model is configured to receive new patient data for another patient and to generate a new treatment plan for the another patient based on the new patient data.

24. The non-transitory computer-readable medium of claim 23, wherein the operations further comprise:
linking the at least one user device portal to a patient identifier, a surgery, and the patient-specific implant for the surgery; and
linking the at least one user device portal to multiple patients for viewing multiple patient data.

25. The non-transitory computer-readable medium of claim 23, wherein the interactive GUI includes a window that concurrently displays an image of a pre-operative pathology of the patient and an image of a post-operative anatomy of the patient for visual comparison by a user associated with the at least one user device portal.

26. The non-transitory computer-readable medium of claim 23, wherein the at least one user device portal includes:
a patient portal for receiving first data from the patient to be added to the case data; and
a healthcare portal for receiving second data from a healthcare provider to be added to the case data.

27. The non-transitory computer-readable medium of claim 23, wherein retraining of the at least one trained machine learning model is based on a similarity score between a modeled result for the treatment plan and an actual post-operative result of the patient.

28. The non-transitory computer-readable medium of claim 23, wherein the patient-specific implant is a cage, a rod, a plate, or a spinal fusion device.

29. The non-transitory computer-readable medium of claim 23, wherein the planned corrected anatomy image includes an image of a virtual model representing an anatomy of the patient in a corrected configuration and annotation for the patient-specific implant.

30. The non-transitory computer-readable medium of claim 23, wherein the viewable image of the virtual model includes at least one of a first image representing pre-operative pathology of the patient or a second image representing a corrected anatomy of the patient.

31. The non-transitory computer-readable medium of claim 23, wherein the operations further comprise:
receiving post-operative data including at least one of a set of post-operative images of the patient, physician feedback, patient recovery level, recovery time, or result after a period of time; and
comparing at least a portion of the post-operative data to the treatment plan, wherein selection of the portion of the received post-operative data as one or more training items is based on the comparison, wherein the one or more training items are inputted into the at least one machine learning model for the retraining.

32. The non-transitory computer-readable medium of claim 23, wherein the operations further comprise:
receiving post-operative data of the patient; and
determining spinal metrics for comparing a pre-operative pathology of the patient, a planned anatomy of the patient, and a post-operative anatomy of the patient, wherein the post-operative anatomy is based on the post-operative data.

33. A computer-implemented method comprising:
providing access, via at least one user device portal of an implant design system, to an interactive graphical user interface (GUI), wherein the implant design system is configured to be used to generate, using at least one trained machine learning model, at least a portion of a treatment plan, wherein the treatment plan includes
a pre-operative pathology of a patient, and
a planned corrected anatomy of the patient after installation of a patient-specific implant;
displaying, via the at least one user device portal, a review interface of the GUI including
a pre-operative pathology image, and
a planned corrected anatomical image and associated planned corrected metrics of the patient, wherein the planned corrected anatomical image shows a virtual model of a spine, in a corrected configuration, with a representation of the patient-specific implant; and
after the patient-specific implant is implanted in the patient,
receiving data associated with a patient outcome of the treatment plan; and
retraining the at least one trained machine learning model based on at least a portion of the data associated with the patient outcome of the treatment plan.

34. The computer-implemented method of claim 33, wherein
the interactive GUI includes a window that concurrently displays an image of a pre-operative pathology of the patient and the planned corrected anatomical image for visual comparison by a user, wherein the interactive GUI includes:
a first button for selecting display of a plurality of pre-operative metrics, and
a second button for selecting display of a plurality of planned post-operative metrics associated with the virtual model.

35. The computer-implemented method of claim 33, wherein the data associated with the patient outcome includes post-operative image data of the patient, the method further comprises determining:
a pre-operative spinal metric for the pre-operative pathology of the patient,
a planned spinal metric of the planned corrected anatomy of the patient represented by the planned corrected anatomical image, and
a post-operative spinal metric based on the post-operative image data.

36. The computer-implemented method of claim 33, further comprising concurrently displaying pre-operative metrics associated with the pre-operative pathology, the planned corrected anatomical image, and the planned corrected metrics.

* * * * *